United States Patent
Wang et al.

(10) Patent No.: US 8,849,679 B2
(45) Date of Patent: Sep. 30, 2014

(54) REMOTE CONTROLLED ROBOT SYSTEM THAT PROVIDES MEDICAL IMAGES

(75) Inventors: Yulun Wang, Goleta, CA (US); Charles S. Jordan, Santa Barbara, CA (US); Marco Pinter, Santa Barbara, CA (US)

(73) Assignee: Intouch Technologies, Inc., Goleta, CA (US)

( * ) Notice: Subject to any disclaimer, the term of this patent is extended or adjusted under 35 U.S.C. 154(b) by 987 days.

(21) Appl. No.: 12/277,842

(22) Filed: Nov. 25, 2008

(65) Prior Publication Data
US 2009/0125147 A1 May 14, 2009

Related U.S. Application Data

(63) Continuation-in-part of application No. 11/542,605, filed on Oct. 2, 2006, now abandoned, which is a continuation-in-part of application No. 11/455,161, filed on Jun. 15, 2006.

(51) Int. Cl.
G06F 3/048 (2013.01)
G06F 19/00 (2011.01)
H04N 7/18 (2006.01)

(52) U.S. Cl.
CPC .................... *H04N 7/185* (2013.01)
USPC .............. 705/2; 700/264; 700/245

(58) Field of Classification Search
USPC ........................................ 705/2
See application file for complete search history.

(56) References Cited

U.S. PATENT DOCUMENTS

| | | | |
|---|---|---|---|
| 4,413,693 A | 11/1983 | Derby | |
| 4,572,594 A | 2/1986 | Schwartz | |
| 4,625,274 A | 11/1986 | Schroeder | |
| 4,638,445 A | 1/1987 | Mattaboni | |
| 4,652,204 A | 3/1987 | Arnett | |
| 4,669,168 A | 6/1987 | Tamura et al. | |
| 4,679,152 A | 7/1987 | Perdue | |
| 4,697,472 A | 10/1987 | Hiyane | |

(Continued)

FOREIGN PATENT DOCUMENTS

| | | |
|---|---|---|
| AU | 1216200 A | 5/2000 |
| CA | 2289697 A1 | 11/1998 |

(Continued)

OTHER PUBLICATIONS

Han, et al., "Construction of an Omnidirectional Mobile Robot Platform Based on Active Dual-Wheel Caster Mechanisms and Development of a Control Simulator", 2000, Kluwer Acedemic Publishers, vol. 29, pp. 257-275.

(Continued)

*Primary Examiner* — Hiep V Nguyen

(57) ABSTRACT

A remote controlled robot system that includes a mobile robot and a remote control station. The mobile robot is controlled by the remote control station and includes a robot monitor, and a robot camera that captures a robot image. The system also includes a medical image device that can be coupled to the robot. The remote control station includes a camera that captures a remote station image, and a monitor that displays the robot image captured by the robot camera in a robot view field, displays the remote station image in a station view field. The robot transmits the robot and medical images to the remote control station such that a larger portion of a network bandwidth is allocated for the medical image than the robot image.

11 Claims, 5 Drawing Sheets

(56) References Cited

U.S. PATENT DOCUMENTS

| | | | |
|---|---|---|---|
| 4,709,265 A | 11/1987 | Silverman et al. |
| 4,751,658 A | 6/1988 | Kadonoff et al. |
| 4,766,581 A | 8/1988 | Korn et al. |
| 4,777,416 A | 10/1988 | George et al. |
| 4,797,557 A | 1/1989 | Ohman |
| 4,803,625 A | 2/1989 | Fu et al. |
| 4,847,764 A | 7/1989 | Halvorson |
| 4,875,172 A | 10/1989 | Kanayama |
| 4,878,501 A | 11/1989 | Shue |
| 4,942,512 A | 7/1990 | Kohno |
| 4,942,538 A | 7/1990 | Yuan et al. |
| 4,953,159 A | 8/1990 | Hayden et al. |
| 4,974,607 A | 12/1990 | Miwa |
| 4,977,971 A | 12/1990 | Crane, III et al. |
| 5,006,988 A | 4/1991 | Borenstein et al. |
| 5,040,116 A | 8/1991 | Evans, Jr. et al. |
| 5,051,906 A | 9/1991 | Evans et al. |
| 5,073,749 A | 12/1991 | Kanayama |
| 5,084,828 A | 1/1992 | Kaufman et al. |
| 5,130,794 A | 7/1992 | Ritchey |
| 5,148,591 A | 9/1992 | Pryor |
| 5,153,833 A | 10/1992 | Gordon et al. |
| 5,155,684 A | 10/1992 | Burke et al. |
| 5,157,491 A | 10/1992 | Kassatly |
| 5,182,641 A | 1/1993 | Diner et al. |
| 5,193,143 A | 3/1993 | Kaemmerer et al. |
| 5,217,453 A | 6/1993 | Wilk |
| 5,224,157 A | 6/1993 | Yamada et al. |
| 5,230,023 A | 7/1993 | Nakano |
| 5,231,693 A | 7/1993 | Backes et al. |
| 5,236,432 A | 8/1993 | Matsen, II et al. |
| 5,315,287 A | 5/1994 | Sol |
| 5,319,611 A | 6/1994 | Korba |
| 5,341,242 A | 8/1994 | Gilboa et al. |
| 5,341,459 A | 8/1994 | Backes |
| 5,347,306 A | 9/1994 | Nitta |
| 5,347,457 A | 9/1994 | Tanaka et al. |
| 5,350,033 A | 9/1994 | Kraft |
| 5,366,896 A | 11/1994 | Margrey et al. |
| 5,374,879 A | 12/1994 | Pin et al. |
| 5,375,195 A | 12/1994 | Johnston |
| 5,417,210 A | 5/1995 | Funda et al. |
| 5,436,542 A | 7/1995 | Petelin et al. |
| 5,441,042 A | 8/1995 | Putman |
| 5,441,047 A | 8/1995 | David et al. |
| 5,442,728 A | 8/1995 | Kaufman et al. |
| 5,462,051 A | 10/1995 | Oka et al. |
| 5,511,147 A | 4/1996 | Abdel-Malek |
| 5,528,289 A | 6/1996 | Cortjens et al. |
| 5,539,741 A | 7/1996 | Barraclough et al. |
| 5,544,649 A | 8/1996 | David et al. |
| 5,550,577 A | 8/1996 | Verbiest et al. |
| 5,553,609 A | 9/1996 | Chen et al. |
| 5,563,998 A | 10/1996 | Yaksich et al. |
| 5,572,229 A | 11/1996 | Fisher |
| 5,572,999 A | 11/1996 | Funda et al. |
| 5,594,859 A | 1/1997 | Palmer et al. |
| 5,600,573 A | 2/1997 | Hendricks et al. |
| 5,636,218 A | 6/1997 | Ishikawa |
| 5,652,849 A | 7/1997 | Conway et al. |
| 5,657,246 A | 8/1997 | Hogan et al. |
| 5,659,779 A | 8/1997 | Laird et al. |
| 5,673,082 A | 9/1997 | Wells et al. |
| 5,675,229 A | 10/1997 | Thorne |
| 5,682,199 A | 10/1997 | Lankford |
| 5,684,695 A | 11/1997 | Bauer |
| 5,701,904 A | 12/1997 | Simmons et al. |
| 5,739,657 A | 4/1998 | Takayama et al. |
| 5,748,629 A | 5/1998 | Caldara et al. |
| 5,749,058 A | 5/1998 | Hashimoto |
| 5,749,362 A | 5/1998 | Funda et al. |
| 5,754,631 A | 5/1998 | Cave |
| 5,758,079 A | 5/1998 | Ludwig et al. |
| 5,762,458 A | 6/1998 | Wang et al. |
| 5,764,731 A | 6/1998 | Yablon |
| 5,767,897 A | 6/1998 | Howell |
| 5,786,846 A | 7/1998 | Hiroaki |
| 5,787,545 A | 8/1998 | Collens |
| 5,802,494 A | 9/1998 | Kuno |
| 5,836,872 A | 11/1998 | Kenet et al. |
| 5,867,653 A | 2/1999 | Aras et al. |
| 5,876,325 A | 3/1999 | Mizuno et al. |
| 5,911,036 A | 6/1999 | Wright et al. |
| 5,917,958 A | 6/1999 | Nunally et al. |
| 5,927,423 A | 7/1999 | Wada et al. |
| 5,949,758 A | 9/1999 | Kober et al. |
| 5,954,692 A | 9/1999 | Smith et al. |
| 5,959,423 A | 9/1999 | Nakanishi et al. |
| 5,961,446 A | 10/1999 | Beller et al. |
| 5,966,130 A | 10/1999 | Benman, Jr. |
| 5,973,724 A | 10/1999 | Riddle |
| 5,974,446 A | 10/1999 | Sonnenreich et al. |
| 5,983,263 A | 11/1999 | Rothrock et al. |
| 5,995,119 A | 11/1999 | Cosatto et al. |
| 5,995,884 A | 11/1999 | Allen et al. |
| 5,999,977 A | 12/1999 | Riddle |
| 6,031,845 A | 2/2000 | Walding |
| 6,047,259 A | 4/2000 | Campbell et al. |
| 6,113,343 A | 9/2000 | Goldenberg et al. |
| 6,133,944 A | 10/2000 | Braun et al. |
| 6,135,228 A | 10/2000 | Asada et al. |
| 6,148,100 A | 11/2000 | Anderson et al. |
| 6,160,582 A | 12/2000 | Hill |
| 6,170,929 B1 | 1/2001 | Wilson et al. |
| 6,175,779 B1 | 1/2001 | Barrett |
| 6,201,984 B1 | 3/2001 | Funda et al. |
| 6,211,903 B1 | 4/2001 | Bullister |
| 6,219,587 B1 | 4/2001 | Ahlin et al. |
| 6,232,735 B1 | 5/2001 | Baba et al. |
| 6,233,504 B1 | 5/2001 | Das et al. |
| 6,233,735 B1 | 5/2001 | Ebihara |
| 6,250,928 B1 | 6/2001 | Poggio et al. |
| 6,256,556 B1 | 7/2001 | Zenke |
| 6,259,806 B1 | 7/2001 | Green |
| 6,259,956 B1 | 7/2001 | Myers et al. |
| 6,266,162 B1 | 7/2001 | Okamura et al. |
| 6,266,577 B1 | 7/2001 | Popp et al. |
| 6,289,263 B1 | 9/2001 | Mukherjee |
| 6,292,713 B1 | 9/2001 | Jouppi et al. |
| 6,304,050 B1 | 10/2001 | Skaar et al. |
| 6,317,652 B1 | 11/2001 | Osada |
| 6,321,137 B1 | 11/2001 | De Smet |
| 6,324,184 B1 | 11/2001 | Hou et al. |
| 6,324,443 B1 | 11/2001 | Kurakake et al. |
| 6,325,756 B1 | 12/2001 | Webb et al. |
| 6,327,516 B1 | 12/2001 | Zenke |
| 6,330,486 B1 | 12/2001 | Padula |
| 6,330,493 B1 | 12/2001 | Takahashi et al. |
| 6,346,950 B1 | 2/2002 | Jouppi |
| 6,346,962 B1 | 2/2002 | Goodridge |
| 6,369,847 B1 | 4/2002 | James et al. |
| 6,381,515 B1 | 4/2002 | Inoue et al. |
| 6,400,378 B1 | 6/2002 | Snook |
| 6,408,230 B2 | 6/2002 | Wada |
| 6,430,471 B1 | 8/2002 | Kintou et al. |
| 6,430,475 B2 | 8/2002 | Okamoto et al. |
| 6,438,457 B1 | 8/2002 | Yokoo et al. |
| 6,445,964 B1 | 9/2002 | White et al. |
| 6,452,915 B1 | 9/2002 | Jorgensen |
| 6,457,043 B1 | 9/2002 | Kwak et al. |
| 6,459,955 B1 | 10/2002 | Bartsch et al. |
| 6,463,352 B1 | 10/2002 | Tadokoro et al. |
| 6,463,361 B1 | 10/2002 | Wang et al. |
| 6,466,844 B1 | 10/2002 | Ikeda et al. |
| 6,468,265 B1 | 10/2002 | Evans et al. |
| 6,470,235 B2 | 10/2002 | Kasuga et al. |
| 6,480,762 B1 | 11/2002 | Uchikubo et al. |
| 6,491,701 B2 | 12/2002 | Tierney et al. |
| 6,496,099 B2 | 12/2002 | Wang et al. |
| 6,496,755 B2 | 12/2002 | Wallach et al. |
| 6,501,740 B1 | 12/2002 | Sun et al. |
| 6,507,773 B2 | 1/2003 | Parker et al. |
| 6,522,906 B1 | 2/2003 | Salisbury et al. |
| 6,523,629 B1 | 2/2003 | Buttz et al. |

(56) References Cited

U.S. PATENT DOCUMENTS

| | | |
|---|---|---|
| 6,526,332 B2 | 2/2003 | Sakamoto et al. |
| 6,529,765 B1 | 3/2003 | Franck et al. |
| 6,529,802 B1 | 3/2003 | Kawakita et al. |
| 6,532,404 B2 | 3/2003 | Colens |
| 6,535,182 B2 | 3/2003 | Stanton |
| 6,535,793 B2 | 3/2003 | Allard |
| 6,540,039 B1 | 4/2003 | Yu et al. |
| 6,543,899 B2 | 4/2003 | Covannon et al. |
| 6,549,215 B2 | 4/2003 | Jouppi |
| 6,563,533 B1 | 5/2003 | Colby |
| 6,580,246 B2 | 6/2003 | Jacobs |
| 6,584,376 B1 | 6/2003 | Van Kommer |
| 6,594,269 B1 | 7/2003 | Polcyn |
| 6,602,469 B1 | 8/2003 | Maus et al. |
| 6,604,019 B2 | 8/2003 | Ahlin et al. |
| 6,604,021 B2 | 8/2003 | Imai et al. |
| 6,611,120 B2 | 8/2003 | Song et al. |
| 6,643,496 B1 | 11/2003 | Shimoyama et al. |
| 6,646,677 B2 | 11/2003 | Noro et al. |
| 6,650,748 B1 | 11/2003 | Edwards et al. |
| 6,684,129 B2 | 1/2004 | Salisbury et al. |
| 6,691,000 B2 | 2/2004 | Nagai et al. |
| 6,710,797 B1 | 3/2004 | McNelley et al. |
| 6,728,599 B2 | 4/2004 | Wang et al. |
| 6,763,282 B2 | 7/2004 | Glenn et al. |
| 6,764,373 B1 | 7/2004 | Osawa et al. |
| 6,769,771 B2 | 8/2004 | Trumbull |
| 6,781,606 B2 | 8/2004 | Jouppi |
| 6,784,916 B2 | 8/2004 | Smith |
| 6,785,589 B2 | 8/2004 | Eggenberger et al. |
| 6,791,550 B2 | 9/2004 | Goldhor et al. |
| 6,798,753 B1 | 9/2004 | Doganata et al. |
| 6,799,065 B1 | 9/2004 | Niemeyer |
| 6,799,088 B2 | 9/2004 | Wang et al. |
| 6,804,580 B1 | 10/2004 | Stoddard et al. |
| 6,804,656 B1 | 10/2004 | Rosenfeld et al. |
| 6,810,411 B1 | 10/2004 | Coughlin et al. |
| 6,836,703 B2 | 12/2004 | Wang et al. |
| 6,839,612 B2 | 1/2005 | Sanchez et al. |
| 6,840,904 B2 | 1/2005 | Goldberg |
| 6,845,297 B2 | 1/2005 | Allard |
| 6,852,107 B2 | 2/2005 | Wang et al. |
| 6,853,878 B2 | 2/2005 | Hirayama et al. |
| 6,853,880 B2 | 2/2005 | Sakagami et al. |
| 6,871,117 B2 | 3/2005 | Wang et al. |
| 6,879,879 B2 | 4/2005 | Jouppi et al. |
| 6,888,333 B2 | 5/2005 | Laby |
| 6,892,112 B2 | 5/2005 | Wang et al. |
| 6,895,305 B2 | 5/2005 | Lathan et al. |
| 6,898,484 B2 | 5/2005 | Lemelson et al. |
| 6,914,622 B1 | 7/2005 | Smith et al. |
| 6,925,357 B2 | 8/2005 | Wang et al. |
| 6,951,535 B2 | 10/2005 | Ghodoussi et al. |
| 6,952,470 B1 | 10/2005 | Tioe |
| 6,957,712 B2 | 10/2005 | Song et al. |
| 6,958,706 B2 | 10/2005 | Chaco et al. |
| 6,965,394 B2 | 11/2005 | Gutta et al. |
| 6,995,664 B1 | 2/2006 | Darling |
| 7,007,235 B1 | 2/2006 | Hussein et al. |
| 7,015,934 B2 | 3/2006 | Toyama et al. |
| RE39,080 E | 4/2006 | Johnston |
| 7,030,757 B2 | 4/2006 | Matsuhira et al. |
| 7,058,689 B2 | 6/2006 | Parker et al. |
| 7,092,001 B2 | 8/2006 | Schulz |
| 7,096,090 B1 | 8/2006 | Zweig |
| 7,115,102 B2 | 10/2006 | Abbruscato |
| 7,117,067 B2 | 10/2006 | McLurkin et al. |
| 7,123,285 B2 | 10/2006 | Smith et al. |
| 7,123,974 B1 | 10/2006 | Hamilton |
| 7,123,991 B2 | 10/2006 | Graf et al. |
| 7,127,325 B2 | 10/2006 | Nagata et al. |
| 7,129,970 B2 | 10/2006 | James et al. |
| 7,133,062 B2 | 11/2006 | Castles et al. |
| 7,142,945 B2 | 11/2006 | Wang et al. |
| 7,142,947 B2 | 11/2006 | Wang et al. |
| 7,151,982 B2 | 12/2006 | Liff et al. |
| 7,154,526 B2 | 12/2006 | Foote et al. |
| 7,155,306 B2 | 12/2006 | Haitin et al. |
| 7,156,809 B2 | 1/2007 | Quy |
| 7,158,859 B2 | 1/2007 | Wang et al. |
| 7,158,860 B2 | 1/2007 | Wang et al. |
| 7,158,861 B2 | 1/2007 | Wang et al. |
| 7,161,322 B2 | 1/2007 | Wang et al. |
| 7,162,338 B2 | 1/2007 | Goncalves et al. |
| 7,164,969 B2 | 1/2007 | Wang et al. |
| 7,164,970 B2 | 1/2007 | Wang et al. |
| 7,167,448 B2 | 1/2007 | Wookey et al. |
| 7,171,286 B2 | 1/2007 | Wang et al. |
| 7,174,238 B1 | 2/2007 | Zweig |
| 7,181,455 B2 | 2/2007 | Wookey et al. |
| 7,184,559 B2 | 2/2007 | Jouppi |
| 7,188,000 B2 | 3/2007 | Chiappetta et al. |
| 7,199,790 B2 | 4/2007 | Rosenberg et al. |
| 7,202,851 B2 | 4/2007 | Cunningham et al. |
| 7,206,627 B2 | 4/2007 | Abovitz et al. |
| 7,215,786 B2 | 5/2007 | Nakadai et al. |
| 7,227,334 B2 | 6/2007 | Yang et al. |
| 7,256,708 B2 | 8/2007 | Rosenfeld |
| 7,262,573 B2 | 8/2007 | Wang et al. |
| 7,289,883 B2 | 10/2007 | Wang et al. |
| 7,292,912 B2 | 11/2007 | Wang et al. |
| 7,317,685 B1 | 1/2008 | Flott et al. |
| 7,321,807 B2 | 1/2008 | Laski |
| 7,346,429 B2 | 3/2008 | Goldenberg et al. |
| 7,382,399 B1 | 6/2008 | McCall |
| 7,386,730 B2 | 6/2008 | Uchikubo |
| 7,391,432 B2 | 6/2008 | Terado |
| 7,400,578 B2 | 7/2008 | Guthrie et al. |
| 7,404,140 B2 | 7/2008 | O'Rourke |
| 7,421,470 B2 | 9/2008 | Ludwig et al. |
| 7,430,209 B2 | 9/2008 | Porter |
| 7,432,949 B2 | 10/2008 | Remy et al. |
| 7,433,921 B2 | 10/2008 | Ludwig et al. |
| 7,441,953 B2 * | 10/2008 | Banks .................. 378/197 |
| 7,492,731 B2 | 2/2009 | Hagendorf |
| 7,523,069 B1 | 4/2009 | Friedl et al. |
| 7,525,281 B2 | 4/2009 | Koyanagi et al. |
| 7,535,486 B2 | 5/2009 | Motomura et al. |
| 7,587,512 B2 | 9/2009 | Ta et al. |
| 7,590,060 B2 | 9/2009 | Miceli |
| 7,593,030 B2 | 9/2009 | Wang et al. |
| 7,599,290 B2 | 10/2009 | Dos Remedios et al. |
| 7,624,166 B2 | 11/2009 | Foote et al. |
| 7,630,314 B2 | 12/2009 | Dos Remedios et al. |
| 7,643,051 B2 | 1/2010 | Sandberg et al. |
| 7,647,320 B2 | 1/2010 | Mok et al. |
| 7,680,038 B1 | 3/2010 | Gourlay |
| 7,693,757 B2 | 4/2010 | Zimmerman |
| 7,698,432 B2 | 4/2010 | Short et al. |
| 7,719,229 B2 | 5/2010 | Kaneko et al. |
| 7,739,383 B1 | 6/2010 | Short et al. |
| 7,756,614 B2 | 7/2010 | Jouppi |
| 7,761,185 B2 | 7/2010 | Wang et al. |
| 7,769,492 B2 | 8/2010 | Wang et al. |
| 7,769,705 B1 | 8/2010 | Luechtefeld |
| 7,813,836 B2 | 10/2010 | Wang et al. |
| 7,831,575 B2 | 11/2010 | Trossell et al. |
| 7,835,775 B2 | 11/2010 | Sawayama et al. |
| 7,860,680 B2 | 12/2010 | Arms et al. |
| 7,890,382 B2 | 2/2011 | Robb et al. |
| 7,912,583 B2 | 3/2011 | Gutmann et al. |
| RE42,288 E | 4/2011 | Degioanni |
| 7,924,323 B2 | 4/2011 | Walker et al. |
| 7,949,616 B2 | 5/2011 | Levy et al. |
| 7,982,763 B2 | 7/2011 | King |
| 7,987,069 B2 | 7/2011 | Rodgers et al. |
| 8,077,963 B2 | 12/2011 | Wang et al. |
| 8,116,910 B2 | 2/2012 | Walters et al. |
| 8,170,241 B2 | 5/2012 | Roe et al. |
| 8,179,418 B2 | 5/2012 | Wright et al. |
| 8,180,486 B2 | 5/2012 | Saito et al. |
| 8,209,051 B2 | 6/2012 | Wang et al. |
| 8,265,793 B2 | 9/2012 | Cross et al. |
| 8,292,807 B2 | 10/2012 | Perkins et al. |

(56) References Cited

U.S. PATENT DOCUMENTS

| | | | |
|---|---|---|---|
| 8,340,654 B2 | 12/2012 | Bratton et al. | |
| 8,340,819 B2 | 12/2012 | Mangaser et al. | |
| 8,463,435 B2 | 6/2013 | Herzog et al. | |
| 8,503,340 B1 | 8/2013 | Xu | |
| 8,527,094 B2 | 9/2013 | Kumar et al. | |
| 8,532,860 B2 | 9/2013 | Daly | |
| 2001/0002448 A1 | 5/2001 | Wilson et al. | |
| 2001/0010053 A1 | 7/2001 | Ben-Shachar et al. | |
| 2001/0020200 A1 | 9/2001 | Das et al. | |
| 2001/0034475 A1 | 10/2001 | Flach et al. | |
| 2001/0034544 A1 | 10/2001 | Mo | |
| 2001/0037163 A1 | 11/2001 | Allard | |
| 2001/0048464 A1 | 12/2001 | Barnett | |
| 2001/0051881 A1 | 12/2001 | Filler | |
| 2001/0054071 A1 | 12/2001 | Loeb | |
| 2001/0055373 A1 | 12/2001 | Yamashita | |
| 2002/0015296 A1 | 2/2002 | Howell | |
| 2002/0027597 A1 | 3/2002 | Sachau | |
| 2002/0027652 A1 | 3/2002 | Paromtchik et al. | |
| 2002/0033880 A1 | 3/2002 | Sul et al. | |
| 2002/0038168 A1 | 3/2002 | Kasuga et al. | |
| 2002/0049517 A1 | 4/2002 | Ruffner | |
| 2002/0055917 A1* | 5/2002 | Muraca | 707/1 |
| 2002/0057279 A1 | 5/2002 | Jouppi | |
| 2002/0058929 A1 | 5/2002 | Green | |
| 2002/0059587 A1 | 5/2002 | Cofano et al. | |
| 2002/0063726 A1 | 5/2002 | Jouppi | |
| 2002/0073429 A1 | 6/2002 | Beane et al. | |
| 2002/0082498 A1 | 6/2002 | Wendt et al. | |
| 2002/0085030 A1 | 7/2002 | Ghani | |
| 2002/0095238 A1 | 7/2002 | Ahlin et al. | |
| 2002/0095239 A1 | 7/2002 | Wallach et al. | |
| 2002/0098879 A1 | 7/2002 | Rheey | |
| 2002/0104094 A1 | 8/2002 | Alexander et al. | |
| 2002/0109770 A1 | 8/2002 | Terada | |
| 2002/0111988 A1 | 8/2002 | Sato | |
| 2002/0120362 A1 | 8/2002 | Lathan et al. | |
| 2002/0130950 A1 | 9/2002 | James et al. | |
| 2002/0133062 A1 | 9/2002 | Arling et al. | |
| 2002/0141595 A1 | 10/2002 | Jouppi | |
| 2002/0143923 A1 | 10/2002 | Alexander | |
| 2002/0177925 A1 | 11/2002 | Onishi et al. | |
| 2002/0183894 A1 | 12/2002 | Wang et al. | |
| 2002/0184674 A1 | 12/2002 | Xi et al. | |
| 2002/0186243 A1 | 12/2002 | Ellis et al. | |
| 2003/0021107 A1 | 1/2003 | Howell et al. | |
| 2003/0030397 A1 | 2/2003 | Simmons | |
| 2003/0048481 A1 | 3/2003 | Kobayashi | |
| 2003/0050733 A1 | 3/2003 | Wang et al. | |
| 2003/0050734 A1 | 3/2003 | Lapham | |
| 2003/0060808 A1 | 3/2003 | Wilk | |
| 2003/0063600 A1 | 4/2003 | Noma et al. | |
| 2003/0069752 A1 | 4/2003 | Ledain et al. | |
| 2003/0100892 A1 | 5/2003 | Morley et al. | |
| 2003/0104806 A1 | 6/2003 | Ruef et al. | |
| 2003/0114962 A1 | 6/2003 | Niemeyer | |
| 2003/0126361 A1 | 7/2003 | Slater et al. | |
| 2003/0135203 A1 | 7/2003 | Wang et al. | |
| 2003/0144579 A1 | 7/2003 | Buss | |
| 2003/0144649 A1 | 7/2003 | Ghodoussi et al. | |
| 2003/0151658 A1 | 8/2003 | Smith | |
| 2003/0152145 A1 | 8/2003 | Kawakita | |
| 2003/0171710 A1 | 9/2003 | Bassuk et al. | |
| 2003/0174285 A1 | 9/2003 | Trumbull | |
| 2003/0180697 A1 | 9/2003 | Kim et al. | |
| 2003/0199000 A1 | 10/2003 | Valkirs et al. | |
| 2003/0206242 A1 | 11/2003 | Choi et al. | |
| 2003/0212472 A1 | 11/2003 | McKee | |
| 2003/0216834 A1 | 11/2003 | Allard | |
| 2003/0220541 A1 | 11/2003 | Salisbury et al. | |
| 2003/0220715 A1 | 11/2003 | Kneifel, II et al. | |
| 2003/0231244 A1 | 12/2003 | Bonilla et al. | |
| 2003/0232649 A1 | 12/2003 | Gizis | |
| 2003/0236590 A1 | 12/2003 | Park et al. | |
| 2004/0001197 A1 | 1/2004 | Ko et al. | |
| 2004/0001676 A1 | 1/2004 | Colgan et al. | |
| 2004/0010344 A1 | 1/2004 | Hiratsuka | |
| 2004/0012362 A1 | 1/2004 | Tsurumi | |
| 2004/0013295 A1 | 1/2004 | Sabe et al. | |
| 2004/0019406 A1* | 1/2004 | Wang et al. | 700/231 |
| 2004/0024490 A1 | 2/2004 | McLurkin et al. | |
| 2004/0041904 A1 | 3/2004 | Lapalme et al. | |
| 2004/0065073 A1 | 4/2004 | Nash | |
| 2004/0068657 A1 | 4/2004 | Alexander et al. | |
| 2004/0078219 A1 | 4/2004 | Kaylor et al. | |
| 2004/0080610 A1 | 4/2004 | James et al. | |
| 2004/0088077 A1 | 5/2004 | Jouppi et al. | |
| 2004/0093409 A1 | 5/2004 | Thompson et al. | |
| 2004/0095516 A1 | 5/2004 | Rohlicek | |
| 2004/0098167 A1 | 5/2004 | Yi et al. | |
| 2004/0102167 A1 | 5/2004 | Shim et al. | |
| 2004/0107254 A1 | 6/2004 | Ludwig et al. | |
| 2004/0107255 A1 | 6/2004 | Ludwig et al. | |
| 2004/0117065 A1 | 6/2004 | Wang et al. | |
| 2004/0123158 A1 | 6/2004 | Roskind | |
| 2004/0135879 A1 | 7/2004 | Stacy et al. | |
| 2004/0138547 A1 | 7/2004 | Wang et al. | |
| 2004/0143421 A1 | 7/2004 | Wang et al. | |
| 2004/0148638 A1 | 7/2004 | Weisman et al. | |
| 2004/0153211 A1 | 8/2004 | Kamoto et al. | |
| 2004/0157612 A1 | 8/2004 | Kim | |
| 2004/0162637 A1 | 8/2004 | Wang et al. | |
| 2004/0167666 A1 | 8/2004 | Wang et al. | |
| 2004/0167668 A1 | 8/2004 | Wang et al. | |
| 2004/0170300 A1 | 9/2004 | Jouppi | |
| 2004/0172301 A1 | 9/2004 | Mihai et al. | |
| 2004/0172306 A1 | 9/2004 | Wohl et al. | |
| 2004/0174129 A1 | 9/2004 | Wang et al. | |
| 2004/0175684 A1 | 9/2004 | Kaasa et al. | |
| 2004/0179714 A1 | 9/2004 | Jouppi | |
| 2004/0186623 A1 | 9/2004 | Dooley et al. | |
| 2004/0189700 A1 | 9/2004 | Mandavilli et al. | |
| 2004/0201602 A1 | 10/2004 | Mody et al. | |
| 2004/0205664 A1 | 10/2004 | Prendergast | |
| 2004/0215490 A1 | 10/2004 | Duchon et al. | |
| 2004/0222638 A1 | 11/2004 | Bednyak | |
| 2004/0224676 A1 | 11/2004 | Iseki | |
| 2004/0230340 A1 | 11/2004 | Fukuchi et al. | |
| 2004/0240981 A1 | 12/2004 | Dothan et al. | |
| 2005/0003330 A1 | 1/2005 | Asgarinejad | |
| 2005/0004708 A1 | 1/2005 | Goldenberg et al. | |
| 2005/0007445 A1 | 1/2005 | Foote et al. | |
| 2005/0013149 A1 | 1/2005 | Trossell | |
| 2005/0021182 A1 | 1/2005 | Wang et al. | |
| 2005/0021183 A1 | 1/2005 | Wang et al. | |
| 2005/0021187 A1 | 1/2005 | Wang et al. | |
| 2005/0021309 A1 | 1/2005 | Alexander et al. | |
| 2005/0024485 A1* | 2/2005 | Castles et al. | 348/14.03 |
| 2005/0027567 A1 | 2/2005 | Taha | |
| 2005/0027794 A1 | 2/2005 | Decker | |
| 2005/0028221 A1 | 2/2005 | Liu et al. | |
| 2005/0035862 A1 | 2/2005 | Wildman et al. | |
| 2005/0038416 A1 | 2/2005 | Wang et al. | |
| 2005/0038564 A1 | 2/2005 | Burick et al. | |
| 2005/0049898 A1 | 3/2005 | Hirakawa | |
| 2005/0052527 A1* | 3/2005 | Remy et al. | 348/14.08 |
| 2005/0060211 A1 | 3/2005 | Xiao et al. | |
| 2005/0065438 A1 | 3/2005 | Miller | |
| 2005/0065659 A1 | 3/2005 | Tanaka et al. | |
| 2005/0065813 A1 | 3/2005 | Mishelevich et al. | |
| 2005/0071046 A1 | 3/2005 | Miyazaki et al. | |
| 2005/0078816 A1 | 4/2005 | Sekiguchi et al. | |
| 2005/0083011 A1 | 4/2005 | Yang et al. | |
| 2005/0099493 A1 | 5/2005 | Chew | |
| 2005/0104964 A1 | 5/2005 | Bovyrin et al. | |
| 2005/0110867 A1 | 5/2005 | Schultz | |
| 2005/0122390 A1 | 6/2005 | Wang et al. | |
| 2005/0125098 A1 | 6/2005 | Wang et al. | |
| 2005/0154265 A1 | 7/2005 | Miro et al. | |
| 2005/0182322 A1 | 8/2005 | Grispo | |
| 2005/0192721 A1 | 9/2005 | Jouppi | |
| 2005/0204438 A1 | 9/2005 | Wang et al. | |
| 2005/0212478 A1 | 9/2005 | Takenaka | |
| 2005/0219356 A1 | 10/2005 | Smith et al. | |

(56) References Cited

U.S. PATENT DOCUMENTS

| | | |
|---|---|---|
| 2005/0225634 A1 | 10/2005 | Brunetti et al. |
| 2005/0231156 A1 | 10/2005 | Yan |
| 2005/0231586 A1 | 10/2005 | Rodman et al. |
| 2005/0232647 A1 | 10/2005 | Takenaka |
| 2005/0234592 A1 | 10/2005 | McGee et al. |
| 2005/0267826 A1 | 12/2005 | Levy et al. |
| 2005/0283414 A1 | 12/2005 | Fernandes et al. |
| 2006/0007943 A1 | 1/2006 | Fellman |
| 2006/0013263 A1 | 1/2006 | Fellman |
| 2006/0013469 A1 | 1/2006 | Wang et al. |
| 2006/0014388 A1 | 1/2006 | Lur et al. |
| 2006/0020694 A1 | 1/2006 | Nag et al. |
| 2006/0029065 A1 | 2/2006 | Fellman |
| 2006/0047365 A1 | 3/2006 | Ghodoussi et al. |
| 2006/0048286 A1 | 3/2006 | Donato |
| 2006/0052676 A1 | 3/2006 | Wang et al. |
| 2006/0052684 A1 | 3/2006 | Takahashi et al. |
| 2006/0064212 A1 | 3/2006 | Thorne |
| 2006/0074525 A1 | 4/2006 | Close et al. |
| 2006/0074719 A1 | 4/2006 | Horner |
| 2006/0082642 A1 | 4/2006 | Wang et al. |
| 2006/0087746 A1 | 4/2006 | Lipow |
| 2006/0095158 A1 | 5/2006 | Lee et al. |
| 2006/0095170 A1 | 5/2006 | Yang et al. |
| 2006/0098573 A1 | 5/2006 | Beer et al. |
| 2006/0103659 A1 | 5/2006 | Karandikar et al. |
| 2006/0104279 A1 | 5/2006 | Fellman et al. |
| 2006/0106493 A1 | 5/2006 | Niemeyer et al. |
| 2006/0122482 A1 | 6/2006 | Mariotti et al. |
| 2006/0125356 A1 | 6/2006 | Meek et al. |
| 2006/0142881 A1 | 6/2006 | Wang et al. |
| 2006/0142983 A1 | 6/2006 | Sorensen |
| 2006/0149418 A1 | 7/2006 | Anvari |
| 2006/0161136 A1 | 7/2006 | Anderson et al. |
| 2006/0161303 A1 | 7/2006 | Wang et al. |
| 2006/0164546 A1 | 7/2006 | Adachi et al. |
| 2006/0171515 A1 | 8/2006 | Hintermeister et al. |
| 2006/0173708 A1 | 8/2006 | Vining et al. |
| 2006/0173712 A1 | 8/2006 | Joubert |
| 2006/0178776 A1 | 8/2006 | Feingold et al. |
| 2006/0178777 A1 | 8/2006 | Park et al. |
| 2006/0189393 A1 | 8/2006 | Edery |
| 2006/0195569 A1 | 8/2006 | Barker |
| 2006/0224781 A1 | 10/2006 | Tsao et al. |
| 2006/0247045 A1 | 11/2006 | Jeong et al. |
| 2006/0259193 A1 | 11/2006 | Wang et al. |
| 2006/0268704 A1 | 11/2006 | Ansari et al. |
| 2006/0271238 A1 | 11/2006 | Choi et al. |
| 2006/0271400 A1 | 11/2006 | Clements et al. |
| 2006/0293788 A1 | 12/2006 | Pogodin |
| 2007/0021871 A1 | 1/2007 | Wang et al. |
| 2007/0025711 A1 | 2/2007 | Marcus |
| 2007/0046237 A1 | 3/2007 | Lakshmanan et al. |
| 2007/0050937 A1 | 3/2007 | Song et al. |
| 2007/0064092 A1 | 3/2007 | Sandberg et al. |
| 2007/0078566 A1 | 4/2007 | Wang et al. |
| 2007/0112700 A1 | 5/2007 | Den et al. |
| 2007/0117516 A1 | 5/2007 | Saidi et al. |
| 2007/0120965 A1 | 5/2007 | Sandberg et al. |
| 2007/0122783 A1 | 5/2007 | Habashi |
| 2007/0133407 A1 | 6/2007 | Choi et al. |
| 2007/0135967 A1 | 6/2007 | Jung et al. |
| 2007/0142964 A1 | 6/2007 | Abramson |
| 2007/0176060 A1 | 8/2007 | White et al. |
| 2007/0192910 A1 | 8/2007 | Vu et al. |
| 2007/0197896 A1 | 8/2007 | Moll et al. |
| 2007/0198128 A1 | 8/2007 | Ziegler et al. |
| 2007/0198130 A1 | 8/2007 | Wang et al. |
| 2007/0199108 A1 | 8/2007 | Angle et al. |
| 2007/0216347 A1 | 9/2007 | Kaneko et al. |
| 2007/0250212 A1 | 10/2007 | Halloran et al. |
| 2007/0255706 A1 | 11/2007 | Iketani et al. |
| 2007/0262884 A1 | 11/2007 | Goncalves et al. |
| 2007/0273751 A1 | 11/2007 | Sachau |
| 2007/0291109 A1 | 12/2007 | Wang et al. |
| 2007/0291128 A1 | 12/2007 | Wang et al. |
| 2008/0009969 A1 | 1/2008 | Bruemmer et al. |
| 2008/0011904 A1 | 1/2008 | Cepollina et al. |
| 2008/0045804 A1 | 2/2008 | Williams |
| 2008/0065268 A1 | 3/2008 | Wang et al. |
| 2008/0082211 A1 | 4/2008 | Wang et al. |
| 2008/0126132 A1 | 5/2008 | Warner et al. |
| 2008/0133052 A1 | 6/2008 | Jones et al. |
| 2008/0174570 A1 | 7/2008 | Jobs et al. |
| 2008/0201016 A1* | 8/2008 | Finlay ............ 700/259 |
| 2008/0201017 A1 | 8/2008 | Wang et al. |
| 2008/0215987 A1 | 9/2008 | Alexander et al. |
| 2008/0229531 A1 | 9/2008 | Takida |
| 2008/0255703 A1 | 10/2008 | Wang et al. |
| 2008/0263451 A1 | 10/2008 | Portele et al. |
| 2008/0269949 A1 | 10/2008 | Norman et al. |
| 2008/0281467 A1 | 11/2008 | Pinter |
| 2008/0306375 A1 | 12/2008 | Sayler et al. |
| 2009/0030552 A1 | 1/2009 | Nakadai et al. |
| 2009/0044334 A1 | 2/2009 | Parsell et al. |
| 2009/0055023 A1 | 2/2009 | Walters et al. |
| 2009/0070135 A1 | 3/2009 | Parida et al. |
| 2009/0086013 A1 | 4/2009 | Thapa |
| 2009/0105882 A1 | 4/2009 | Wang et al. |
| 2009/0106679 A1 | 4/2009 | Anzures et al. |
| 2009/0122699 A1 | 5/2009 | Alperovitch et al. |
| 2009/0125147 A1 | 5/2009 | Wang et al. |
| 2009/0144425 A1 | 6/2009 | Marr et al. |
| 2009/0164255 A1 | 6/2009 | Menschik et al. |
| 2009/0164657 A1 | 6/2009 | Li et al. |
| 2009/0171170 A1 | 7/2009 | Li et al. |
| 2009/0177323 A1 | 7/2009 | Ziegler et al. |
| 2009/0177641 A1 | 7/2009 | Raghavan |
| 2009/0237317 A1 | 9/2009 | Rofougaran |
| 2009/0240371 A1 | 9/2009 | Wang et al. |
| 2009/0248200 A1 | 10/2009 | Root |
| 2009/0259339 A1 | 10/2009 | Wright et al. |
| 2010/0010672 A1 | 1/2010 | Wang et al. |
| 2010/0010673 A1 | 1/2010 | Wang et al. |
| 2010/0019715 A1 | 1/2010 | Roe et al. |
| 2010/0051596 A1 | 3/2010 | Diedrick et al. |
| 2010/0063848 A1 | 3/2010 | Kremer et al. |
| 2010/0070079 A1 | 3/2010 | Mangaser et al. |
| 2010/0073490 A1 | 3/2010 | Wang et al. |
| 2010/0076600 A1 | 3/2010 | Cross et al. |
| 2010/0085874 A1 | 4/2010 | Noy et al. |
| 2010/0088232 A1 | 4/2010 | Gale |
| 2010/0115418 A1 | 5/2010 | Wang et al. |
| 2010/0116566 A1 | 5/2010 | Ohm et al. |
| 2010/0131103 A1 | 5/2010 | Herzog et al. |
| 2010/0145479 A1 | 6/2010 | Griffiths |
| 2010/0157825 A1 | 6/2010 | Anderlind et al. |
| 2010/0191375 A1 | 7/2010 | Wright et al. |
| 2010/0228249 A1 | 9/2010 | Mohr et al. |
| 2010/0268383 A1 | 10/2010 | Wang et al. |
| 2010/0323783 A1 | 12/2010 | Nonaka et al. |
| 2011/0050841 A1 | 3/2011 | Wang et al. |
| 2011/0071702 A1 | 3/2011 | Wang et al. |
| 2011/0172822 A1 | 7/2011 | Ziegler et al. |
| 2011/0187875 A1 | 8/2011 | Sanchez et al. |
| 2011/0190930 A1 | 8/2011 | Hanrahan et al. |
| 2011/0213210 A1 | 9/2011 | Temby et al. |
| 2011/0218674 A1 | 9/2011 | Stuart et al. |
| 2011/0245973 A1 | 10/2011 | Wang et al. |
| 2011/0292193 A1 | 12/2011 | Wang et al. |
| 2011/0301759 A1 | 12/2011 | Wang et al. |
| 2012/0023506 A1 | 1/2012 | Maeckel et al. |
| 2012/0036484 A1 | 2/2012 | Zhang et al. |
| 2012/0072023 A1 | 3/2012 | Ota |
| 2012/0072024 A1 | 3/2012 | Wang et al. |
| 2012/0092157 A1 | 4/2012 | Tran |
| 2012/0095352 A1 | 4/2012 | Tran |
| 2012/0191246 A1 | 7/2012 | Roe et al. |
| 2012/0191464 A1 | 7/2012 | Stuart et al. |

FOREIGN PATENT DOCUMENTS

| | | |
|---|---|---|
| CN | 1554193 A | 12/2004 |
| CN | 1554985 A | 12/2004 |

(56) References Cited

FOREIGN PATENT DOCUMENTS

| | | |
|---|---|---|
| CN | 101106939 A | 1/2008 |
| CN | 101390098 A | 3/2009 |
| CN | 101507260 A | 8/2009 |
| CN | 101730894 A | 6/2010 |
| CN | 101866396 A | 10/2010 |
| CN | 101978365 A | 2/2011 |
| CN | 102203759 A | 9/2011 |
| CN | 101106939 B | 11/2011 |
| EP | 92/466492 A2 | 1/1992 |
| EP | 92/488673 A2 | 6/1992 |
| EP | 0981905 B1 | 1/2002 |
| EP | 1 262 142 A2 | 12/2002 |
| EP | 1304872 A1 | 4/2003 |
| EP | 1 536 660 B2 | 9/2004 |
| EP | 1 536 660 A2 | 6/2005 |
| EP | 2005/1573406 A2 | 9/2005 |
| EP | 2005/1594660 A2 | 11/2005 |
| EP | 1763243 A2 | 3/2007 |
| EP | 2007/1791464 A2 | 6/2007 |
| EP | 2007/1800476 A2 | 6/2007 |
| EP | 1819108 A2 | 8/2007 |
| EP | 2007/1856644 A2 | 11/2007 |
| EP | 1536660 A3 | 4/2008 |
| EP | 2008/1928310 A2 | 6/2008 |
| EP | 1232610 B1 | 1/2009 |
| EP | 20092027716 A2 | 2/2009 |
| EP | 2010/2145274 A1 | 1/2010 |
| EP | 2010/2214111 A2 | 8/2010 |
| EP | 2010/2263158 A2 | 12/2010 |
| EP | 2011/2300930 A2 | 3/2011 |
| EP | 2300930 A1 | 3/2011 |
| EP | 2011/2342651 A2 | 7/2011 |
| GB | 2431261 A | 4/2007 |
| JP | 07-194609 A | 8/1995 |
| JP | 2007-213753 A | 8/1995 |
| JP | 2007-248823 A | 8/1995 |
| JP | 2007-257422 A | 10/1995 |
| JP | 08084328 A | 3/1996 |
| JP | H0884328 | 3/1996 |
| JP | 96/8320727 A | 12/1996 |
| JP | 9-267276 A | 10/1997 |
| JP | 10079097 A | 3/1998 |
| JP | 10288689 A | 10/1998 |
| JP | 2000-032319 A | 1/2000 |
| JP | 2000/049800 A | 2/2000 |
| JP | 2000/079587 A | 3/2000 |
| JP | 2000/196876 A | 7/2000 |
| JP | 2000-235423 A | 8/2000 |
| JP | 2001/188124 A | 4/2001 |
| JP | 2001/125641 A | 5/2001 |
| JP | 2001-147718 A | 5/2001 |
| JP | 2001/179663 A | 7/2001 |
| JP | 2001-198865 A | 7/2001 |
| JP | 2001-198868 A | 7/2001 |
| JP | 2001-199356 A | 7/2001 |
| JP | 2002-000574 A | 1/2002 |
| JP | 2002-046088 A | 2/2002 |
| JP | 2002/112970 A | 4/2002 |
| JP | 2002/101333 A | 5/2002 |
| JP | 2002-305743 A | 10/2002 |
| JP | 2002-355779 A | 12/2002 |
| JP | 2004/524824 T | 8/2004 |
| JP | 2004-261941 A | 9/2004 |
| JP | 2004/289379 A | 10/2004 |
| JP | 2005/028066 A | 2/2005 |
| JP | 2005/059170 A | 3/2005 |
| JP | 2006/508806 A | 3/2006 |
| JP | 2006/109094 A | 4/2006 |
| JP | 2006/224294 A | 8/2006 |
| JP | 2006/246438 A | 9/2006 |
| JP | 2007-007040 A | 1/2007 |
| JP | 2007/081646 A | 3/2007 |
| JP | 2007/232208 A | 9/2007 |
| JP | 2007-316966 A | 12/2007 |
| JP | 2010/064154 A | 3/2010 |
| JP | 2010/532109 A | 9/2010 |
| JP | 2010/246954 A | 11/2010 |
| KR | 2006/0037979 A | 5/2006 |
| KR | 2009/0012542 A | 2/2009 |
| KR | 2010/0019479 A | 2/2010 |
| KR | 2010/0139037 A | 12/2010 |
| WO | WO 93-06690 A1 | 4/1993 |
| WO | WO 98-51078 A | 11/1998 |
| WO | WO 99/67067 A1 | 12/1999 |
| WO | 00/25516 A1 | 5/2000 |
| WO | 00/33726 A3 | 6/2000 |
| WO | 01/31861 A1 | 5/2001 |
| WO | WO 03/077745 A | 9/2003 |
| WO | 2004/008738 A1 | 1/2004 |
| WO | 2004/012018 A2 | 2/2004 |
| WO | WO 2004/075456 A2 | 9/2004 |
| WO | 2006/012797 A1 | 2/2006 |
| WO | 2006/078611 A1 | 4/2006 |
| WO | 2006044847 A2 | 4/2006 |
| WO | WO 2007/041295 A1 | 9/2006 |
| WO | 2007/041295 A2 | 4/2007 |
| WO | 2007/041038 A1 | 6/2007 |
| WO | 2008/100272 A2 | 8/2008 |
| WO | 2008/100272 A3 | 10/2008 |
| WO | 2009/117274 A2 | 9/2009 |
| WO | 2009/128997 A1 | 10/2009 |
| WO | 2009/145958 A2 | 12/2009 |
| WO | 2010/006205 A1 | 1/2010 |
| WO | 2010/006211 A1 | 1/2010 |
| WO | 2010/033666 A1 | 3/2010 |
| WO | 2010/047881 A1 | 4/2010 |
| WO | 2010/062798 A1 | 6/2010 |
| WO | 2010/065257 A1 | 6/2010 |
| WO | 2010/120407 A1 | 10/2010 |
| WO | 2011/028589 A2 | 3/2011 |
| WO | 2011/028589 A3 | 4/2011 |
| WO | 2011/097130 A2 | 8/2011 |
| WO | 2011/097132 A2 | 8/2011 |
| WO | 2011/109336 A2 | 9/2011 |
| WO | 2011/097132 A3 | 12/2011 |
| WO | 2011/149902 A2 | 12/2011 |

OTHER PUBLICATIONS

Haule et al., "Control Scheme for Delayed Teleoperation Tasks", May 17, 1995, Proceedings of the Pacific Rim Conference on Communications, Computer and Signal Processing.

Lee et al., "A novel method of surgical instruction: International telementoring", 1998, Internet pp. 1-4.

Ogata et al., "Emotional Communication Robot: WAMOEBA-2R—Emotion Model and Evaluation Experiments", 1999, Internet, pp. 1-16.

Rovetta et al., "A New Telerobotic Application: Remote Laparoscopic Surgery Using Satellites and Optical Fiber Networks for Data Exchange", Jun. 1, 1996, International Journal of Robotics Research, pp. 267-279.

Tahboub, Karim A. et al., "Dynamics Analysis and Control of a Holonomic Vehicle With Continously Variable Transmission", Mar. 2002, Journal of Dynamic Systems, Measurement, and Control, ASME vol. 124, pp. 118-126.

Yamauchi et al., PackBot: A Versatile Platform for Military Robotics, 2004, Internet, pp. 1-10.

International Search Report received for International Patent Application No. PCT/US2007/14099, mailed on Jul. 30, 2008, 1 page.

International Preliminary Report on Patentability and Written Opinion received for International Patent Application No. PCT/US/200714099, dated Dec. 16, 2008, 5 pages.

Al-Kassab, "A Review of Telemedicine", Journal of Telemedicine and Telecare, 1999, vol. 5, Supplement 1.

F. Ando et al., "A Multimedia Self-service Terminal with Conferencing Functions", 1995, IEEE, pp. 357-362.

Android Amusement Corp., "What Marketing Secret", 1982 http:///www.theoldrobots.com/images17/dc8.JPG.

Applebome, "Planning Domesticated Robots for Tomorrow's Household", New York Times, Mar. 4, 1982, pp. 21 and 23 http://www.theoldrobots.com/images17/dc17.JPG.

(56) References Cited

OTHER PUBLICATIONS

Baltus et al., "Towards Personal Service Robots for the Elderly, Proceedings for the Elderly Workshop on Interactive Robots and Entertainment", 2000, Computer Science and Robotics, http://www.cs.cmu.edu/thrun/papers/thrun.nursebot-early.pdf.
Bar-Cohen et al., Virtual reality robotic telesurgery simulations using MEMICA haptic system, Mar. 5, 2001, Internet, pp. 1-7.
Bartholomew, "An Apothecary's Pharmacy", 1230-1240 http://classes.bnf.fr/ema/grands/034.htm.
Bauer, Jeffrey C., "Service Robots in Health Care: The Evolution of Mechanical Solutions to Human Resource Problems", Jun. 2003.
Bauer, John et al., "Remote telesurgical mentoring: feasibility and efficacy", 2000, IEEE, pp. 1-9.
Bischoff, "Design Concept and Realization of the Humanoid Service Robot HERMES", Field and Service Robotics, Springer, London, 1998, pp. 485-492.
Blackwell, Gerry, "Video: A Wireless LAN Killer App?", 2002, Internet pp. 1-3.
Breslow, Michael J., MD et al., "Effect of a multiple-site intensive care unit telemedicine program on clinical and economic outcome: An alternative paradigm for intensivist staffing", Critical Care Med, Jan. 2004, vol. 32, No. 1, pp. 31-38.
Brooks, Rodney, Abstracts from Flesh & Machines, How Robots Will Change Us, "Remote Presence", p. 131-147, Feb. 2002.
Candelas Herias, F.A. et al., "Flexible virtual and remote laboratory for teaching Robotics", Formatex 2006, Proc. Advance in Control Education, Madrid, Spain, Jun. 21-23, 2006.
Celi et al., "The eICU: It's not just telemedicine", Critical Care Medicine, vol. 29, No. 8 (Supplement), Aug. 2001.
Cheetham, Anastasia et al., "Interface Development for a Child's Video Conferencing Robot", 2000, pp. 1-4.
Cleary et al., "State of the art in surgical robotics: Clinical applications and technology challenges", Feb. 24, 2002 Internet, pp. 1-26.
CNN, "Floating 'droids' to roam space corridors of the future", Jan. 12, 2000, Internet, pp. 1-4.
CNN.com/Technology,"Paging R.Robot: Machine helps doctors with patients", Sep. 30, 2003, Internet, 1-3.
Crowley, "Hello to Our Future", AARP Bulletin, Jan. 2000 http://www.cs.cmu.ed/-nursebot/web/press/aarp_99_14/millennium.html.
Dalton, "Techniques for Web Telerobotics", PhD thesis, University of Western Australia, 2001, http://telerobot.mech.uwa.edu.au/information.html, http://catalogue.library.uwa.edu.au/search.
Davies, "Robotics in Minimally Invasive Surgery", 1995, Internet, pp. 5/1-5/2.
DiGiorgio, James, "Is Your Emergency Department of the 'Leading Edge'?", 2005, Internet, pp. 1-4.
Discovery Channel Canada, "Inventing the Future: 2000 Years of Discovery", Jan. 2, 2000 (Video/Transcript).
Elhajj et al., "Supermedia in Internet-based telerobotic operations", 2001, Internet, pp. 1-14.
Elhajj et al., "Synchronization and Control of Supermedia Transmission Via the Internet", Proceedings of 2001 International Symposium on Intelligent Multimedia, Video and Speech Processing, May 2-4, 2001, Hong Kong.
Ellison et al., "Telerounding and Patient Satisfaction Following Surgery".
Fels, "Developing a Video-Mediated Communication System for Hospitalized Children", Telemedicine Journal, vol. 5, No. 2, 1999.
Fetterman, Videoconferencing over the Internet, 2001, Internet, pp. 1-8.
Fiorini, "Health Care Robotics: A Progress Report, IEEE International Conference on Robotics and Automation", 1997.
Ghiasi, "A Generic Web-based Teleoperations Architecture: Details and Experience", SPIE Conference on Telemanipulator and Telepresence Technologies VI, Sep. 1999.
Goldberg et al., "Collaborative Teleoperation via the Internet", IEEE International Conference on Robotics and Automation, Apr. 2000, San Francisco, California.
Goldberg, "Desktop Teleoperation via the World Wide Web, Proceedings of the IEEE International Conference on Robotics and Automation", 1995, http://citeseer.ist.psu.edu/cache/papers/cs/5/ftp:zSzzSzusc.eduzSzpubzSziriszSzraiders.pdf/go1.
Goldberg, "More Online Robots, Robots that Manipulate", Internet, Updated Aug. 2001 http://ford.ieor.berkeley.edu/ir/robots_a2.html.
Goldman, Lea, "Machine Dreams", Entrepreneurs, Forbes, May 27, 2002.
Gump, Michael D., "Robot Technology Improves VA Pharmacies", 2001, Internet, pp. 1-3.
Handley, "RFC 2327—SDP: Session Description Protocol", Apr. 1998 http://www.faqs.org/rfcs/rfc2327.html.
Hanebeck, "ROMAN: a mobile Robotic Assistant for Indoor Service Applications", Proceedings of the 1997 IEEE/RSJ International Conference on Intelligent Robots and Systems, 1997.
Harmo et al., "Moving Eye—Interactive Telepresence Over Internet With a Ball Shaped Mobile Robot", 2000.
Hees, William P., "Communications Design for a Remote Presence Robot", Jan. 14, 2002.
Holmberg, "Development of a Holonomic Mobile Robot for Mobile Manipulation Tasks", International Conference on Field and Service Robotics, Pittsburgh, PA, Aug. 1999.
Ishiguro, "Integrating a Perceptual Information Infrastructure with Robotic Avatars: A Framework for Tele-Existence" Proceeding of IEEE Conference on Intelligent Robots and Systems, http://www.ai.soc.i.kyoto-u.ac.jp/services/publications/99/99conf/07.pdf.
Ishihara, Ken et al., "Intelligent Microrobot DDS (Drug Delivery System) Measured and Controlled by Ultrasonics", Nov. 3-May 1991, IEEE/RSJ, pp. 1145-1150, vol. 2.
Itu, "ITU-T H.323 Packet-based multimedia communications", ITU, Feb. 1998, http://www.itu.int/rec/T-REC-H.323-199802-S/en.
Ivanova, Natali, "Master's thesis: Internet Based Interface for Control of a Mobile Robot", Department of Numerical Analysis and Computer Science.
Jenkins, "Telehealth Advancing Nursing Practice", Nursing Outlook, Mar./Apr. 2001, vol. 49, No. 2.
Johanson, Supporting video-mediated communication over the Internet, Chalmers University of Technology, Dept of Computer Engineering, Gothenburg, Sweden, 2003.
Jouppi, et al., "Mutually-Immersive Audio Telepresence", Audio Engineering Society Convention Paper, presented at $113^{th}$ Convention Oct. 2002.
Jouppi, Norman P., "First Steps Towards Mutually-Immersive Mobile Telepresence", CSCW '02, Nov. 16-20, 2002, New Orleans LA.
Kanehiro, Fumio et al., Virtual Humanoid Robot Platform to Develop Controllers of Real Humanoid Robots without Porting, 2001, IEEE, pp. 3217-3276.
Kaplan et al., "An Internet Accessible Telepresence".
Keller et al., "Raven Interface Project", Fall 2001 http://upclose.lrdc.pitt.edu/people/louw_assets/Raven_Slides.pps.
Khatib, "Robots in Human Environments", Proc. International Conference on Control, Automation, Robotics, and Vision, ICRACV2000, Dec. 2000, Singapore, pp. 454-457.
Kuzuoka et al., "Can the GestureCam Be a Surrogate?".
Lane, "Automated Aides", Newsday, Oct. 17, 2000, http://www.cs.cum.edu/-nursebot/web/press/nd4380.htm.
Lim, Hun-ok et al., Control to Realize Human-like Walking of a Biped Humanoid Robot, IEEE 2000, pp. 3271-3276.
Linebarger, John M. et al., "Concurrency Control Mechanisms for Closely Coupled Collaboration in Multithreaded Virtual Environments", Presence, Special Issue on Advances in Collaborative VEs (2004).
Loeb, Gerald, "Virtual Visit: Improving Communication for Those Who Need It Most", 2001.
Long, "HelpMate Robotics, Inc. (Formerly Transitions Research Corporation) Robot Navigation Technology", NIST Special Publication 950-1, Mar. 1999, http://www.atp.nist.gov/eao/sp950-1/helpmate.htm.
Luna, Nancy, "Robot a new face on geriatric care", OC Register, Aug. 6, 2003.
Mack, "Minimally invasive and robotic surgery", 2001, Internet IEEE, pp. 568-572.

(56) References Cited

OTHER PUBLICATIONS

Mair, Telepresence—The Technology and Its Economic and Social Implications, IEEE Technology and Society, 1997.
Martin, Anya, "Days Ahead", Assisted Living Today, vol. 9, Nov/Dec 2002, pp. 19-22.
Barrett, "Video Conferencing Business Soars as Companies Cut Travel; Some Travel Cuts Are Permanent", http://www.ivci.com/international_videoconferencing_news_videoconferencing_news_19.html, Mar. 13, 2002.
Brooks, "A Robust Layered Control System for a Mobile Robot," IEEE Journal of Robotics and Automation, 2 (1), Mar. 1986, 10 pgs.
Davis, "Meet iRobot, the Smartest Webcam on Wheels," Wired Magazine, 8.09, http://www.wired.com/wired/archive/8.09/irobot_pr.html, Sep. 2000, 2 pgs.
Dean, et al., "1992 AAAI Robot Exhibition and Competition," AI Magazine, Spring 1993, 10 pgs.
Defendant VGo Communications, Inc.'s Invalidity Contentions Pursuant to the Feb. 27, 2012 Civil Minute Order, May 2, 2012.
Defendant-Counterclaimant VGo Communications, Inc.'s Supplemental Invalidity Contentions Pursuant to the Feb. 27, 2012 Civil Minute Order, May 14, 2012.
Dudenhoeffer, et al., "Command and Control Architectures for Autonomous Micro-Robotic Forces", http://www.inl.gov/technicalpublications/Documents/3157051.pdf, Apr. 2001.
Elhajj, "Real-Time Haptic Feedback in Internet-Based Telerobotic Operation", IEEE International Conference on Electro/Information Technology, http://www.egr.msu.edu/~ralab-web/cgi_bin/internet-teleoperation.php, Jun. 2000.
Fong, "Collaborative Control: A Robot-Centric Model for Vehicle Teleoperation", The Robotics Institute Carnegie Mellon University, http://web.archive.org/web/20030504040803/www.ricmu.edu/cgi-bin/tech_reports.cgi?year=2001&text=0, Nov. 2001.
Goldenberg, et al., "Telemedicine in Otolaryngology", American Journal of Otolaryngology vol. 23,No. 1, 2002 , pp. 35-43.
Grow, "Office Coworker Robot," Time Magazine, http://www.time.com/time/specials/packages/article/0,28804,1936165_1936255_1936640,00.html, Nov. 19, 2001, 2 pgs.
Itu, "ITU-T H.281 A Far End Camera Control Protocol for Videoconferences using H.224", http://www.itu.int/rec/T-RECH.281-199411-I/en, Nov. 1994.
Itu, "ITU-T H.450.11 Call Intrusion Supplementary Service for H.323", http://www.itu.int/rec/T-RECH.450.11-200103-I/en, Mar. 2001.
Itu, "ITU-T H.450.9 Call Completion Supplementary Services for H.323", http://www.itu.int/rec/T-RECH.450.9-200011-I/en, Nov. 2000.
Knight, et al., "Active Visual Alignment of a Mobile Stereo Camera Platform", Proceedings of the IEEE, International Conference on Robotics and Automation, San Francisco, Apr. 24-28, 2000, pp. 3202-3208.
Metz, "HP Labs", pcmag.com, http://www.pcmag.com/article2/0,2817,1130820,00.asp, Jul. 1, 2003.
PictureTel Adds New Features and Functionality to Its Award-Winning Live200 Desktop Videoconferencing System, PR Newswire Association, LLC, Gale, Cengage Learning, http://www.thefreelibrary.com/PictureTel+Adds+New+Features+And+Functionality+To+Its+Award-Winning . . . -a019512804, Jun. 13, 1997.
Picturetel, "PictureTel Live200 for Windows NT Product Guide", http://support.polycom.com/global/documents/support/user/products/video/live200_live200NT_product_guide.pdf, Nov. 1994.
Roach, "Automatic Call Back Service in SIP", http://tools.ietf.org/pdf/draftroach-sip-acb-00.pdf, Mar. 2000.
Summers, "Microsoft NetMeeting 3 Features excerpt from Official Microsoft NetMeeting 3.0 Book", http://technet.microsoft.com/en-us/library/cc723477.aspx#XSLTsection121121120120, excerpt from Microsoft Press http://www.computerbooksonline.com/abook.asp?i=0735605823, Mar. 1999.
U.S. Appl. No. 10/783,760, filed Feb. 20, 2004, Wang, et al., 48 pgs.
U.S. Appl. No. 60/449,762, filed Feb. 24, 2003, Wang, et al., 28 pgs.

Weiss, et al., "Pebbles: A Personal Technology for Meeting Education, Social and Emotional Needs of Hospitalised Children", Personal and Ubiquitous Computing 5, Springer-Verlag London Ltd., 2001, pp. 157-168.
Zambroski, "CMU, Pitt Developing 'nursebot'", http://www.cs.cmu.edu/~nursebot/web/press/tribunereview.html, Oct. 27, 2000.
Blaer, et al., "TopBot: Automated Network Topology Detection With a Mobile Robot", Proceedings of the 2003 IEEE International Conference on Robotics 7 Automation, Taipei, Taiwan, Sep. 14-19, 2003, pp. 1582-1587.
Bradner, "The Internet Standards Process—Revision 3", Network Working Group Request for Comments: 2026, www.rfc-e ditor.org!rfC/rfc2026. txt, Oct. 1996, pp. 1-36.
Christensen et al., "BeeSoft User's Guide and Reference", Robots for the Real World™, Real World Interface, Inc., www.praecogito.com/-brudy/zaza/BeeSoft-manual-1.2-2/ beeman~1.htm, Sep. 26, 1997, pp. 1-203.
Dario, "A Robot Workstation for Diagnosis and Physical Therapy", IEEE Catalog No. 88TH0234-5, 1989, pp. 67-72.
Gump, "Robot Technology Improves VA Pharmacies", Internet, 2001, pp. 1-3.
Leifer, et al., "VIPRR: A Virtually in Person Rehabilitation Robot", Proceedings of 1997 International Conference on Rehabilitation Robotics, http://www.stanford.edu/group/rrdlPeople/vdl/publicationsIICORR97/VIPRR.html, Apr. 14-15, 1997, 4 pgs.
Minsky "Telepresence", Omni, Jun. 1980, pp. 1-6.
Motorola Technical Developments, et al., "Detection of Target Mobile Signal Strength", PriorArt Database: Technical Disclosure, IP.com, Retrieved from http:www.ip.com/pubview/IPCOM000009024D, original publication date: Jan. 1, 1999 by Motorola, Inc., pp. 205-206, Aug. 1, 2002, pp. 1583-1587.
Noritsugu, "Application of Rubber Artificial Muscle Manipulator as a Rehabilitation Robot", IEEE/ASME Transactions on Mechatronics, vol. 2, No. 4, Dec. 1997, pp. 259-267.
Reynolds et al., "Review of Robotic Telemedicine Utilization in Intensive Care Units (ICUs)", 11th Annual ATA Symposium, Tampa, Florida, 2011, 1 pg.
"Saphira Software Manual", Saphira Version 5.3, ActiveMedia, Inc., 1997, 105 pgs.
Tipsuwan, et al., "Gain Adaptation of Networked Mobile Robot to Compensate QoS Deterioration", IEEE, 2000, pp. 3146-3151.
Tsui, et al., "Exploring Use Cases for Telepresence Robots", Human-Robot Interaction, Lausanne, Switzerland, http://robotics.cs.uml.edu/fileadmin/content/publications/2011/tsui-et-al-telepresence-HRI11.pdf, Robotics Lab UMass Lowell, 2011, 7 pgs.
Umass Lowell Robotics Lab, "Robotics Lab @ UMASS Lowell", Brochure, http://robotics.cs.uml.edu/fileadmin/content/brochures/roboticslab_brochure_2011_WEB.pdf, 2011, 2 pgs.
Appeal from the U.S. District Court for the Central District of California in case No. 11-cv-9185, Judge Percy Anderson, Joint Appendix, vol. I of IV, Jun. 24, 2013, pp. A1-A6357.
Appeal from the U.S. District Court for the Central District of California in case No. 11-cv-9185, Judge Percy Anderson, Joint Appendix, vol. II of IV, Jun. 24, 2013, pp. A6849-A10634.
Appeal from the U.S. District Court for the Central District of California in case No. 11-cv-9185, Judge Percy Anderson, Joint Appendix, vol. III of IV, Jun. 24, 2013, pp. A10654-A15517.
Appeal from the U.S. District Court for the Central District of California in case No. 11-cv-9185, Judge Percy Anderson, Joint Appendix, vol. IV of IV, Jun. 24, 2013, pp. A15677-A18127.
Brief for Defendant-Appellee VGO Communications, Inc., Appeal from the U.S. District Court for the Central District of California, in Case No. 2:11-cv-9185, Judge Percy Anderson, May 28, 2013, 75 pages.
Civil Minutes-General: Case No. CV 11-9185PA (AJWx), *InTouch Tech., Inc.* v. *VGo Commons, Inc.*, Sep. 10, 2012, 7 pages.
Office Action received for Chinese Patent Application No. 200680044698.0, Nov. 4, 2010, 9 pages of Official Copy and 15 pages of English Translation.
Opening Brief for Plaintiff-Appellant InTouch Technologies, Inc., Appeal from the U.S. District Court for the Central District of California in Case No. 11-cv-9185, Judge Percy Anderson, Apr. 12, 2013, 187 pages.

(56) References Cited

OTHER PUBLICATIONS

Reply Brief for Plaintiff-Appellant InTouch Technologies, Inc., Appeal from the U.S. District Court for the Central District of California in Case No. 11-cv-9185, Judge Percy Anderson, Jun. 14, 2013, 39 pages.
Activmedia Robotics, "Pioneer 2/PeopleBot, Operations Manual, Version 9", Oct. 2001, 78 pages.
Weaver et al., "Monitoring and Control Using the Internet and Java", vol. 3, Proceedings of the 25th Annual Conference of the IEEE Industrial Electronics Society, 1999, pp. 1152-1158.
Apple Inc., "I Phone", iPhone Series XP-002696350, pp. 1-29.
"Magne Charge", Smart Power for Electric Vehicles, General Motors Corporation, Serial No. 75189637, Registration No. 2114006, Filing Date: Oct. 29, 1996, Aug. 26, 1997, 2 pages.
"Using your Infrared Cell Phone Camera", Available on <http://www.catsdomain.com/xray/about.htm>, retrieved on Jan. 23, 2014, Courtesy of Internet Wayback Machine, Jan. 30, 2010, 4 pages.
Gostai "Gostai Jazz: Robotic Telepresence", available online at <http://www.gostai.com>, 4 pages.
Jacobs et al., "Applying Telemedicine to Outpatient Physical Therapy", AMIA, Annual Symposium Proceedings, 2002, 1 page.
Kurlowicz et al., "The Mini Mental State Examination (MMSE)", The Hartford Institute for Geriatric Nursing, Journal of Psychiatric Research, No. 3, Jan. 1999, 2 pages.
Lemaire, Edward, "Using Communication Technology to Enhance Rehabilitation Services", Terry Fox Mobile Clinic, The Rehabilitation Centre, Ottawa, Canada, Version 2.0, 1998-2001, 104 pages.
Nakazato et al., "Group-Based Interface for Content-Based Image Retrieval", Proceedings of the Working Conference on Advanced Visual Interfaces, 2002, pp. 187-194.
Nakazato et al., "Group-Oriented User Interface for Digital Image Management", Journal of Visual Languages and Computing, vol. 14, No. 4, Aug. 2003, pp. 45-46.
North, Michael, "Telemedicine: Sample Script and Specifications for a Demonstration of Simple Medical Diagnosis and Treatment Using Live Two-Way Video on a Computer Network", Greenstar Corporation, 1998, 5 pages.
Piquepaille, Roland, "How New Technologies are Modifying Our Way of Life", Roland Piquepaille's Technology Trends, This Blog and its RSS Feed Are Moving, Oct. 31, 2004, 2 pages.
Radvision, "Making Sense of Bandwidth the NetSense Way", Network Congestion in Unmanaged Networks Bandwidth Estimation and Adaptation Techniques, Radvision's Netsense Technology, 2010, 7 pages.
Roy et al., "Towards Personal Service Robots for the Elderly", Workshop on Interactive Robots and Entertainment (Wire 2000), vol. 25, Apr. 30-May 1, 2000, 7 pages.
Theodosiou et al., "MuLVAT: A Video Annotation Tool Based on XML-Dictionaries and Shot Clustering", 19th International Conference, Artificial Neural Networks-ICANN, Sep. 14-17, 2009, pp. 913-922.
Tyrrell et al., "Teleconsultation in Psychology: The Use of Videolinks for Interviewing and Assessing Elderly Patients", British Geriatrics Society, Age and Ageing, vol. 30, No. 3, May 2001, pp. 191-195.
Telepresence Research, Inc., "Telepresence Mobile Robot System", available online at <http://www. telepresence.com/telepresence-research/TELEROBOT/>, retrieved on Nov. 23, 2010, Feb. 20, 1995, 3 pages.
Adams, Chris, "Simulation of Adaptive Behavior (SAB'02)—From Animals to Animats 7", Mobile Robotics Research Group, The Seventh International Conference, available online at: <http://www.dai.ed.ac.uk/groups/mrg/MRG.html>, retrieved on Jan. 22, 2014, Aug. 4-11, 2002, 1 page.
Evans et al., "HelpMate: The Trackless Robotic Courier", PYXIS, available online at <http://www.pyxis.com/>, 3 pages.
Gaidioz et al., "Synchronizing Network Probes to Avoid Measurement Intrusiveness with the Network Weather Service", High-Performance Distributed Computing, Proceedings of the Ninth International Symposium, 2000, pp. 147-154.
Garner et al., "The Application of Telepresence in Medicine", BT Technology Journal, vol. 15, No. 4, Oct. 1, 1997, pp. 181-187.
McCardle et al., "The challenge of utilizing new technology in design education", 2000 Internet, pp. 122-127.
Meng, "E-Service Robot in Home Healthcare", Proceedings of the 2000, IEEE/RSJ, International Conference on Intelligent Robots and Systems, 2000.
Michaud, Introducing 'Nursebot', The Boston Globe, Sep. 11, 2001, pp. 1-5, http://www.cs.cmu.edu/nursebot/web/press/globe_3_01/index.html.
Mobile Robotics Research Group, "Mobile Robotics Research Group", 2000 Internet, pp. 1-2, Edinburgh.
Montemerlo, "Telepresence: Experiments in Next Generation Internet", CMU Robotics Institute, Oct. 20, 1998, http://www.ri.cmu.edu/creative/archives.htm (Video/Transcript).
Murphy, "Introduction to A1 Robotics", 2000.
Nakajima et al., "A Multimedia Teleteaching System sing an Electronic Whiteboard for Two-Way Communication of Motion Videos and Chalkboards", 1993, IEEE, pp. 436-441.
"National Energy Research Scientific Computing Center, Berkeley Lab's RAGE Telepresence Robot Captures R&D100 Award", Jul. 2, 2002, http://www.nersc.gov/news/newsroom/RAGE070202.php.
Nomadic Technologies, Inc., "Nomad XR4000 Hardware Manual", Mar. 1999.
Ogata et al., "Development of Emotional Communication Robot: WAMOEBA-2r—Esperimental evaluation . . . ", 2000 IEEE, pp. 175-180.
Oh, "Autonomous Battery Recharging for Indoor Mobile Robots", Proceedings of Australian Conference on Robotics and Automation, 2000, http://users.rsise.anu.edu.au/rsl/rsl_papers/ACRA2000/Auto_Recharge_Paper.pdf.
Ojha, Anad, "An application of Virtual Reality in Rehabilitation", Jan. 1994, IEEE, pp. 4-6.
Paulos et al., "A World Wide Web Telerobotic Remote Environment Browser", http://vive.cs.berkeley.edu/capek, 1995.
Paulos, "Designing Personal Tele-embodiment", IEEE International Conference on Robotics and Automation, 1998, http://www.prop.org/papers/icra98.pdf.
Paulos, Eric John, "Personal Tele-Embodiment", UC Berkeley, Fall 2001.
Paulos, "PRoP: Personal Roving Presence", ACM:CHI Proceedings of CHI '98, http://www.prop.org/papers/chi98.pdf.
Paulos, Video of PRoP 2 at Richmond Field Station, www.prop.org. May 2001, Printout of Home Page of Website and two-page Transcript of the audio portion of said PRoP Video.
Paulos, et al. , "Ubiquitous Tele-embodiment: Applications and Implications", International Journal of Human Computer Studies, Jun. 1997, vol. 46, No. 6, pp. 861-877.
Pin et al., "A New Family of Omnidirectional and Holonomic Wheeled Platforms for Mobile Robots", IEEE, vol. 10, No. 4, Aug. 1994.
Roy et al., "Towards Personal Service Robots for the Elderly", Internet, Mar. 7, 2002.
Salemi et al, "MILO: Personal robot platform", 2005, Internet, pp. 1-6.
Sandt, Frederic et al., "Perceptions for a Transport Robot in Public Environments", 1997, IROS '97.
Schaeffer, "Care-O-bot: A System for Assisting Elderly or Disabled Persons in Home Environments", Proceedings of AAATE-99, 1999, http://morpha.de/download/publications/IPA_Systems_For_AssistingElderly_or_DisabledPersons_AAATE1999.pdf.
Schultz, "Web Interfaces for Mobile Robots in Public Places", Robotics & Automation magazine, IEEE, vol. 7, Issue 1, Mar. 2000.
Shimoga et al., Touch and force reflection for telepresence surgery, 1994, IEEE, pp. 1049-1050.
Siegwart, "Interacting Mobile Robots on the Web", Proceedings of the 1999 IEEE International Conference on Robotics and Automation, May 1999.
Simmons, "Xavier: An Autonomous Mobile Robot on the Web", IEE robotics and Automation Magazine, 1999, pp. 43-48.

(56) References Cited

OTHER PUBLICATIONS

Spawar Systems Center, "Robart", 1998, San Diego, CA, http://web.archive.org/web/*/http://www.nosc.mil/robots/land/robart/robart.html http://web.archive.org/web/19981202205636/http://www.nosc.mil/robots/land/robart/robart.html.

Stephenson, Gary, "Dr. Robot Tested at Hopkins", Aug. 5, 2003, Internet, pp. 1-2.

Stoianovici et al., "Robotic Tools for Minimally Invasive Urologic Surgery", Dec. 2002, Internet, 1-17.

Suplee, "Mastering the Robot", The Washington Post, p. A01, Sep. 17, 2000 http://www.cs.cmu.edu-nursebot/web/press/wash/index.html.

Tendick et al., "Human-Machine Interfaces for Minimally Invasive Surgery", 1997, IEEE, pp. 2771-2776.

Thrun et al, "Probabilistic Algorithms and the Interactive Museum Tour-Guide Robot Minerva", 2000, Internet pp. 1-35.

Tzafestas, et al., "VR-based Teleoperation of a Mobile Robotic Assistant: Progress Report", 2000, Internet, pp. 1-23.

Urquhart, Kim, "InTouch's robotic Companion 'beams up' healthcare experts", Medical Device Daily, vol. 7, No. 39, Feb. 27, 2003, p. 1, 4.

Weiss et al., Telework and video-mediated communication: Importance of real-time, interactive communication for workers with disabilities, pp. 1-4, California State University Northridge, http://www.csun.edu/cod/conf/1999/proceedings/session0238.html.

West et al., "Design of Ball Wheel Mechanisms for Omnidirectional Vehicles with Full Mobility and Invariant Kinematics", Journal of Mechanical Design, vol. 119, pp. 153-161, Jun. 1997.

Yamasaki et al., Applying Personal Robots and Active Interface to Video Conference Systems, 1995, Internet, pp. 243-248.

Yong et al., "Robot task execution with telepresence using virtual reality technology", 1998, Internet, pp. 1-9.

Zamrazil, Kristie, "Telemedicine in Texas: Public Policy Concerns", House Research Organization Focus Report, Texas House of Representatives, No. 76-22, May 5, 2000 http://www.hro.house.state.tx.us/focus/telemed.pdf.

Zipperer, Lorri, "Robotic dispensing system", 1999, Internet, pp. 1-2.

Zorn, Benjamin G., "Ubiquitous Telepresence", http://www.cs.colorado.edu/~zorn/ut/vision/vision.html, Mar. 5, 1996.

\* cited by examiner

US 8,849,679 B2

REMOTE CONTROLLED ROBOT SYSTEM THAT PROVIDES MEDICAL IMAGES

CROSS-REFERENCE TO RELATED APPLICATION

This application is a continuation-in-part of U.S. application Ser. No. 11/542,605, filed on Oct. 2, 2006, pending, which is as a continuation-in-part of U.S. application Ser. No. 11/455,161, filed on Jun. 15, 2006.

BACKGROUND OF THE INVENTION

1. Field of the Invention

The subject matter disclosed generally relates to the field of mobile two-way teleconferencing.

2. Background Information

There has been marketed a mobile robot introduced by InTouch Technologies, Inc., the assignee of this application, under the trademarks COMPANION, RP-6 and RP-7. The InTouch robot is controlled by a user at a remote station. The remote station may be a personal computer with a joystick that allows the user to remotely control the movement of the robot. Both the robot and remote station have cameras, monitors, speakers and microphones to allow for two-way video/audio communication. The robot camera provides video images to a screen at the remote station so that the user can view the robot's surroundings and move the robot accordingly.

The InTouch robot can be used by medical personnel to monitor and interact with a patient. For example, a doctor can move the robot into a patient's room and utilize the two-way videoconferencing capabilities of the system to examine the patient. Examination of the patient is limited to visual inspection and audio feedback. It would be desirable if the system would also allow other devices to be used to examine and interact with a patient.

BRIEF SUMMARY OF THE INVENTION

A remote controlled robot system that includes a mobile robot and a remote control station. The mobile robot is controlled by the remote control station and includes a robot monitor, and a robot camera that captures a robot image. The system also includes a medical image device that can be coupled to the robot. The remote control station includes a camera that captures a remote station image, and a monitor that displays the robot image captured by the robot camera in a robot view field, displays the remote station image in a station view field. The robot transmits the robot and medical images to the remote control station such that a larger portion of a network bandwidth is allocated for the medical image than the robot image.

DETAILED DESCRIPTION

Disclosed is a remote controlled robot system that includes a mobile robot and a remote control station. The mobile robot is controlled by the remote control station and includes a robot monitor, and a robot camera that captures a robot image. The system also includes a medical image device that can be coupled to the robot. The remote control station includes a camera that captures a remote station image, and a monitor that displays the robot image captured by the robot camera in a robot view field, displays the remote station image in a station view field. The robot transmits the robot and medical images to the remote control station such that a larger portion of a network bandwidth is allocated for the medical image than the robot image. A medical personnel at the remote control station can interact with another personnel at the robot site to move the medical image device to vary the captured images. The system allows the remote operator to conduct a video conference with someone at the robot site while viewing medical images in real time.

Figure 1:
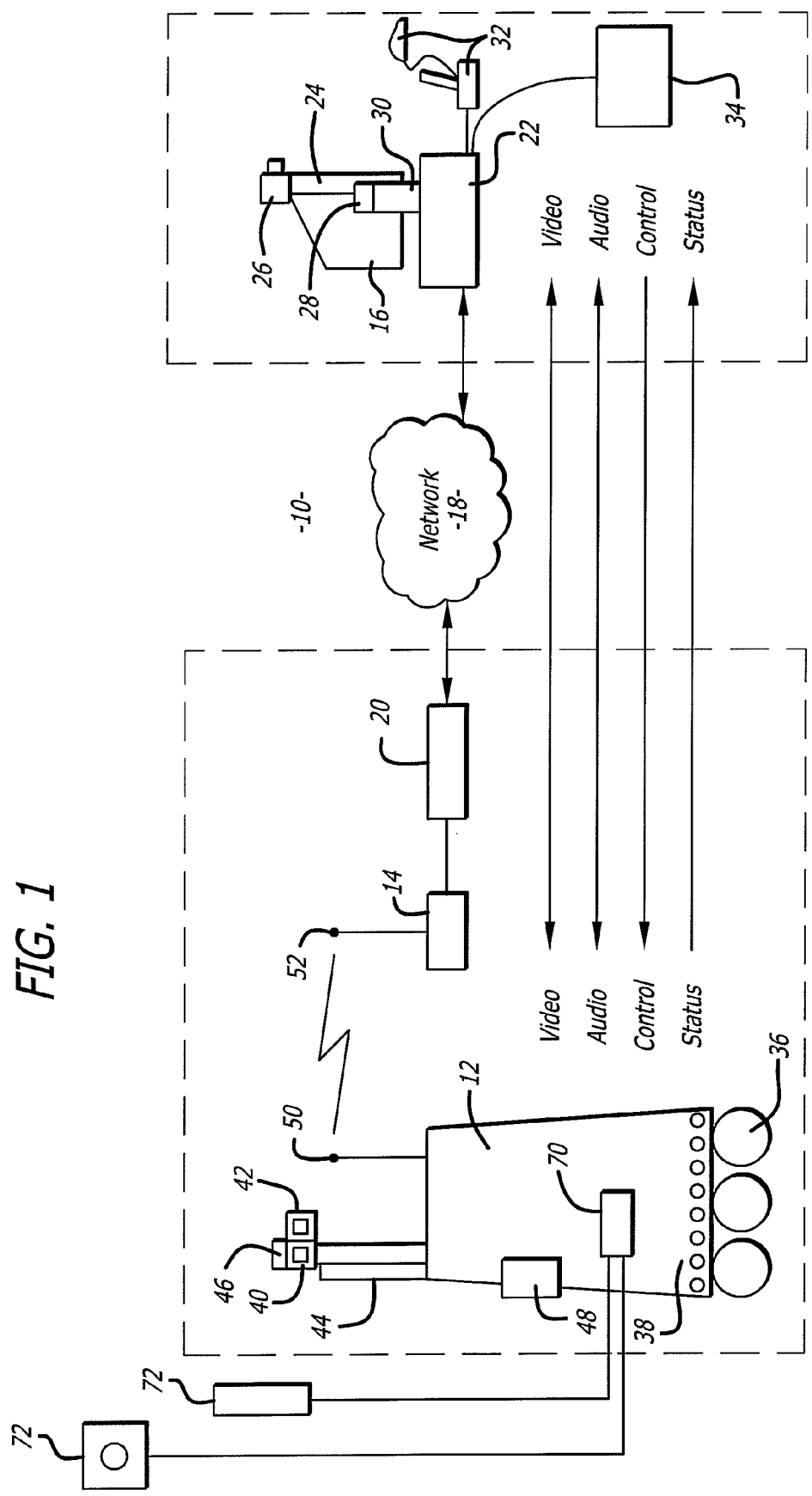
FIG. 1 is an illustration of a robotic system.

Referring to the drawings more particularly by reference numbers, FIG. 1 shows a robotic system 10 that can be used to conduct a remote visit. The robotic system 10 includes a robot 12, a base station 14 and a remote control station 16. The remote control station 16 may be coupled to the base station 14 through a network 18. By way of example, the network 18 may be either a packet switched network such as the Internet, or a circuit switched network such has a Public Switched Telephone Network (PSTN) or other broadband system. The base station 14 may be coupled to the network 18 by a modem 20 or other broadband network interface device. By way of example, the base station 14 may be a wireless router. Alternatively, the robot 12 may have a direct connection to the network thru for example a satellite.

The remote control station 16 may include a computer 22 that has a monitor 24, a camera 26, a microphone 28 and a speaker 30. The computer 22 may also contain an input device 32 such as a joystick and/or a mouse and a keyboard 34. The control station 16 is typically located in a place that is remote from the robot 12. Although only one remote control station 16 is shown, the system 10 may include a plurality of remote stations. In general any number of robots 12 may be controlled by any number of remote stations 16 or other robots 12. For example, one remote station 16 may be coupled to a plurality of robots 12, or one robot 12 may be coupled to a plurality of remote stations 16, or a plurality of robots 12.

Each robot 12 includes a movement platform 36 that is attached to a robot housing 38. Also attached to the robot housing 36 is a pair of cameras 40 and 42, a monitor 44, a microphone(s) 46 and a speaker(s) 48. The microphone 46 and speaker 30 may create a stereophonic sound. The robot 12 may also have an antenna 50 that is wirelessly coupled to an antenna 52 of the base station 14. The robot monitor 44 and cameras 40 and 82 move together in two degrees of freedom including pan and tilt directions. The system 10 allows a user at the remote control station 16 to move the robot 12 through operation of the input device 32. The robot cameras 40 and 42 are coupled to the remote monitor 24 so that a user at the remote station 16 can view a patient. Likewise, the robot monitor 44 is coupled to the remote camera 26 so that the patient can view the user. The microphones 28 and 46, and speakers 30 and 48, allow for audible communication between the patient and the user.

Camera 40 may provide a wide angle view. Conversely, camera 42 may contain a zoom lens to provide a narrow angle view. Camera 42 can capture a zoom image that is transmitted to the remote control station. Camera 40 can capture a non-zoom image that can be transmitted to the remote control station. Although two cameras are shown and described, it is to be understood that the robot may contain only one camera that has the capability to provide a zoom image and a non-zoom image.

The remote station computer 22 may operate Microsoft OS software and WINDOWS XP or other operating systems such as LINUX. The remote computer 22 may also operate a video driver, a camera driver, an audio driver and a joystick driver. The video images may be transmitted and received with compression software such as MPEG CODEC.

The robot 12 may include an auxiliary video port 70. The auxiliary video port 70 may include USB, VGA, Y-video/audio electrical connectors and associated electronic circuitry. A plurality of video devices 72 can be connected to one or more of the ports 70. By way of example, the video devices 72 may include an ultrasound device, an otoscope, a echocardiogram, a dermatology camera, a ceiling camera and/or a video playback machine such as a VCR or DVD player. The video devices 72 capture video that is transmitted to the remote station 16 through the mobile robot 12. By way of example, the ultrasound device may capture images of a patient that are then transmitted to the remote control station 16 and displayed by the station monitor 24. The video devices 72 can be coupled to the robot with either a wire or through a wireless connection. For purposes of this patent an auxiliary port will describe both wireless and wired connections between a video device and the robot.

Figure 2:
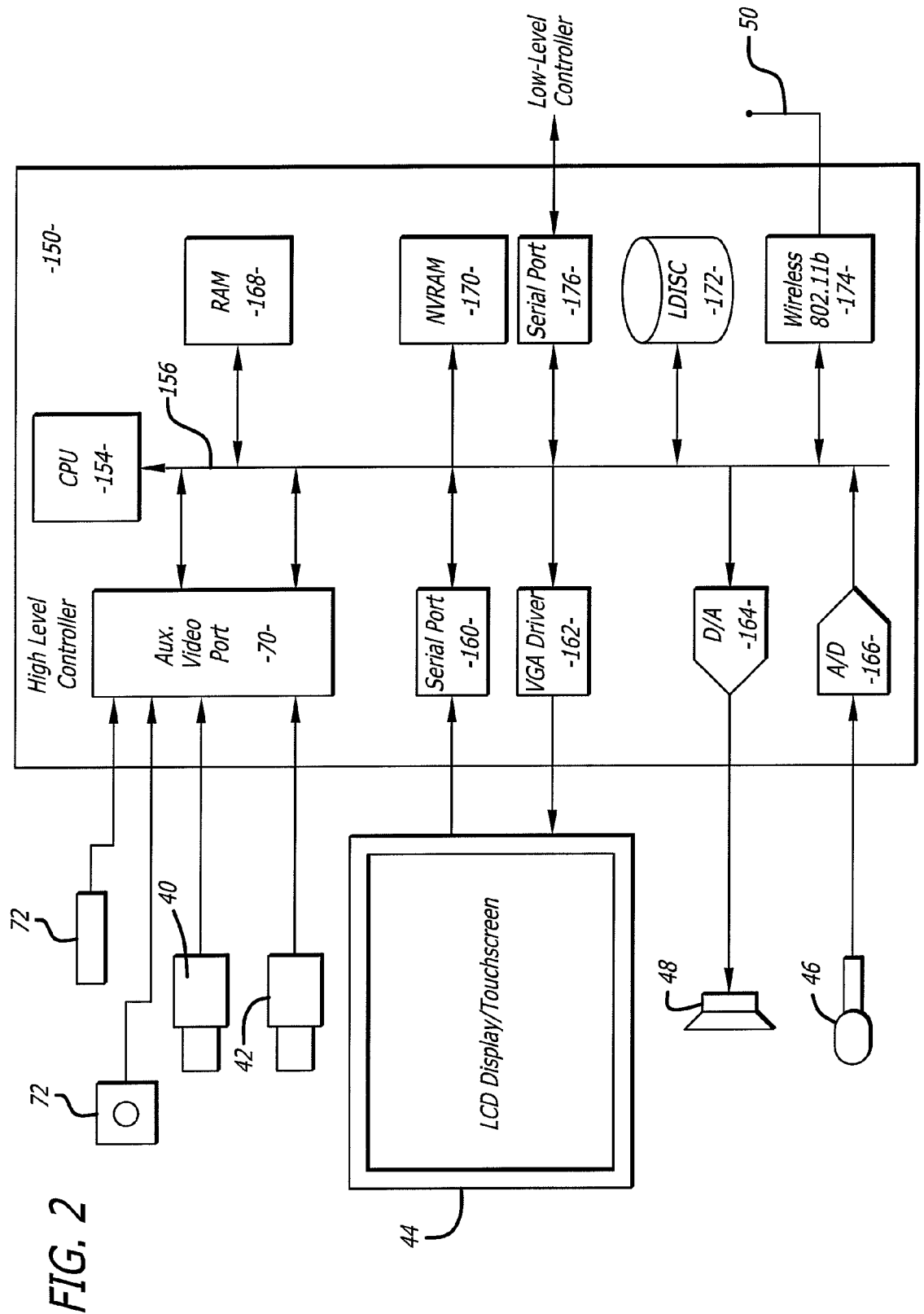
FIG. 2 is a schematic of an electrical system of a robot.
Figure 3:
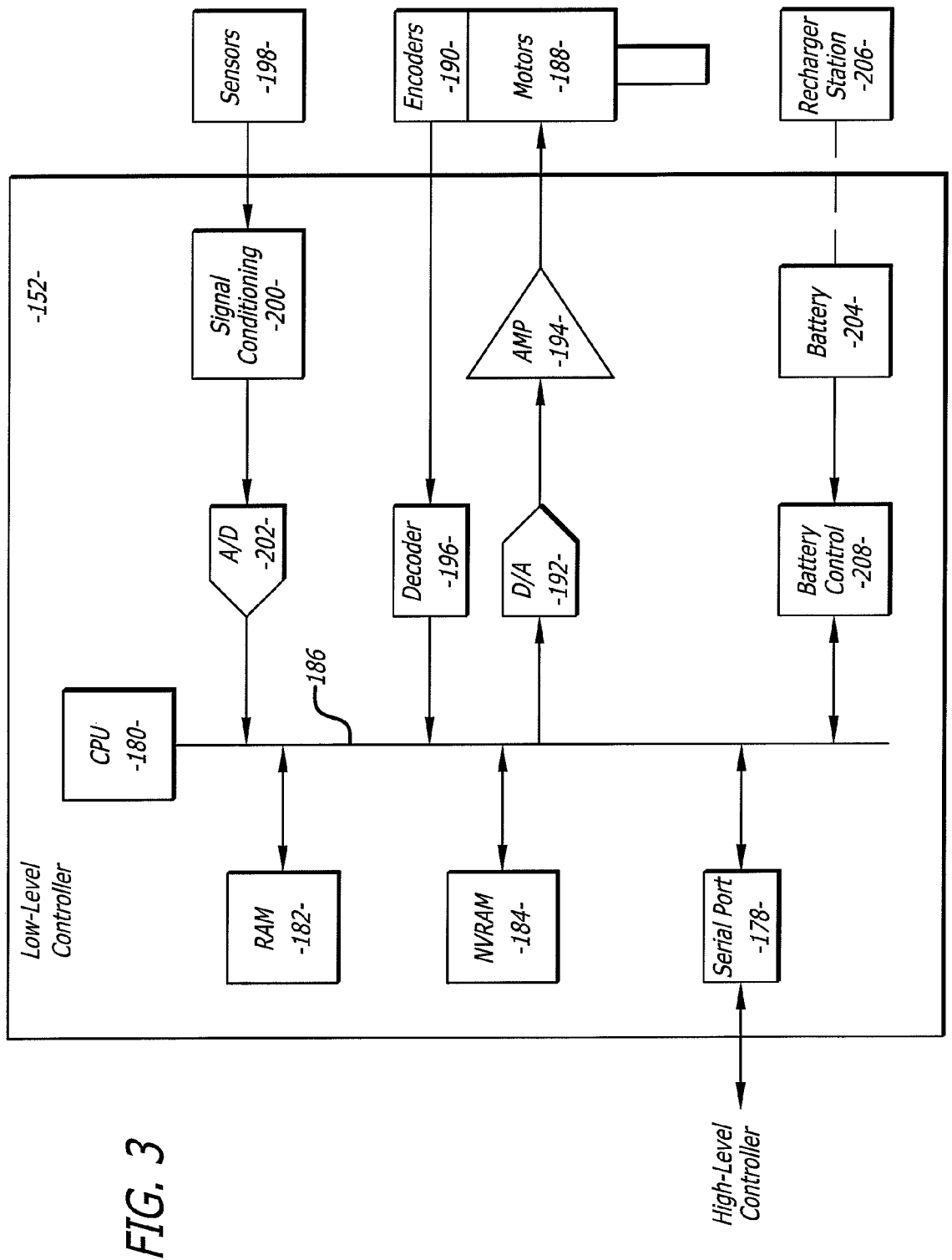
FIG. 3 is a further schematic of the electrical system of the robot.

FIGS. 2 and 3 show an embodiment of a robot 12. Each robot 12 may include a high level control system 150 and a low level control system 152. The high level control system 150 may include a processor 154 that is connected to a bus 156. The auxiliary video port 70 is coupled to the robot cameras 40 and 42 and the external video devices 72. The port 70 may include a frame grabber that has multiple composite video inputs that allow the robot to capture video from the cameras 40 and 42 and the video devices 72. The port 70 provides video from one of the video devices, or cameras 40 or 42, based on input from the remote control station 16. For example, the port 70 may feed video from camera 40 and then switch the feed to one of the video devices 72.

The monitor 44 is coupled to the bus 156 by a serial output port 160 and a VGA driver 162. The monitor 44 may include a touchscreen function that allows the patient to enter input by touching the monitor screen.

The speaker 48 is coupled to the bus 156 by a digital to analog converter 164. The microphone 46 is coupled to the bus 156 by an analog to digital converter 166. The high level controller 150 may also contain random access memory (RAM) device 168, a non-volatile RAM device 170 and a mass storage device 172 that are all coupled to the bus 156. The mass storage device 172 may contain medical files of the patient that can be accessed by the user at the remote control station 16. For example, the mass storage device 172 may contain a picture of the patient. The user, particularly a health care provider, can recall the old picture and make a side by side comparison on the monitor 24 with a present video image of the patient provided by the camera 40. The robot antennae 50 may be coupled to a wireless transceiver 174. By way of example, the transceiver 174 may transmit and receive information in accordance with IEEE 802.11b.

The controller 154 may operate with a LINUX OS operating system. The controller 154 may also operate MS WINDOWS along with video, camera and audio drivers for communication with the remote control station 16. Video information may be transceived using MPEG CODEC compression techniques. The software may allow the user to send e-mail to the patient and vice versa, or allow the patient to access the Internet. In general the high level controller 150 operates to control communication between the robot 12 and the remote control station 16.

The remote control station 16 may include a computer that is similar to the high level controller 150. The computer would have a processor, memory, I/O, software, firmware, etc. for generating, transmitting, receiving and processing information.

The high level controller 150 may be linked to the low level controller 152 by serial ports 176 and 178. The low level controller 152 includes a processor 180 that is coupled to a RAM device 182 and non-volatile RAM device 184 by a bus 186. Each robot 12 contains a plurality of motors 188 and motor encoders 190. The motors 188 can actuate the movement platform and move other parts of the robot such as the monitor and camera. The encoders 190 provide feedback information regarding the output of the motors 188. The motors 188 can be coupled to the bus 186 by a digital to analog converter 192 and a driver amplifier 194. The encoders 190 can be coupled to the bus 186 by a decoder 196. Each robot 12 also has a number of proximity sensors 198 (see also FIG. 1). The position sensors 198 can be coupled to the bus 186 by a signal conditioning circuit 200 and an analog to digital converter 202.

The low level controller 152 runs software routines that mechanically actuate the robot 12. For example, the low level controller 152 provides instructions to actuate the movement platform to move the robot 12. The low level controller 152 may receive movement instructions from the high level controller 150. The movement instructions may be received as movement commands from the remote control station or another robot. Although two controllers are shown, it is to be understood that each robot 12 may have one controller, or more than two controllers, controlling the high and low level functions.

The various electrical devices of each robot 12 may be powered by a battery(ies) 204. The battery 204 may be recharged by a battery recharger station 206 (see also FIG. 1). The low level controller 152 may include a battery control circuit 208 that senses the power level of the battery 204. The low level controller 152 can sense when the power falls below a threshold and then send a message to the high level controller 150.

The system 10 may be the same or similar to a robotic system provided by the assignee InTouch-Health, Inc. of Santa Barbara, Calif. under the name RP-6 or RP-7. The system may also be the same or similar to the system disclosed in U.S. Pat. No. 6,925,357 issued to Wang et al. on Aug. 2, 2005, which is hereby incorporated by reference.

Figure 4:
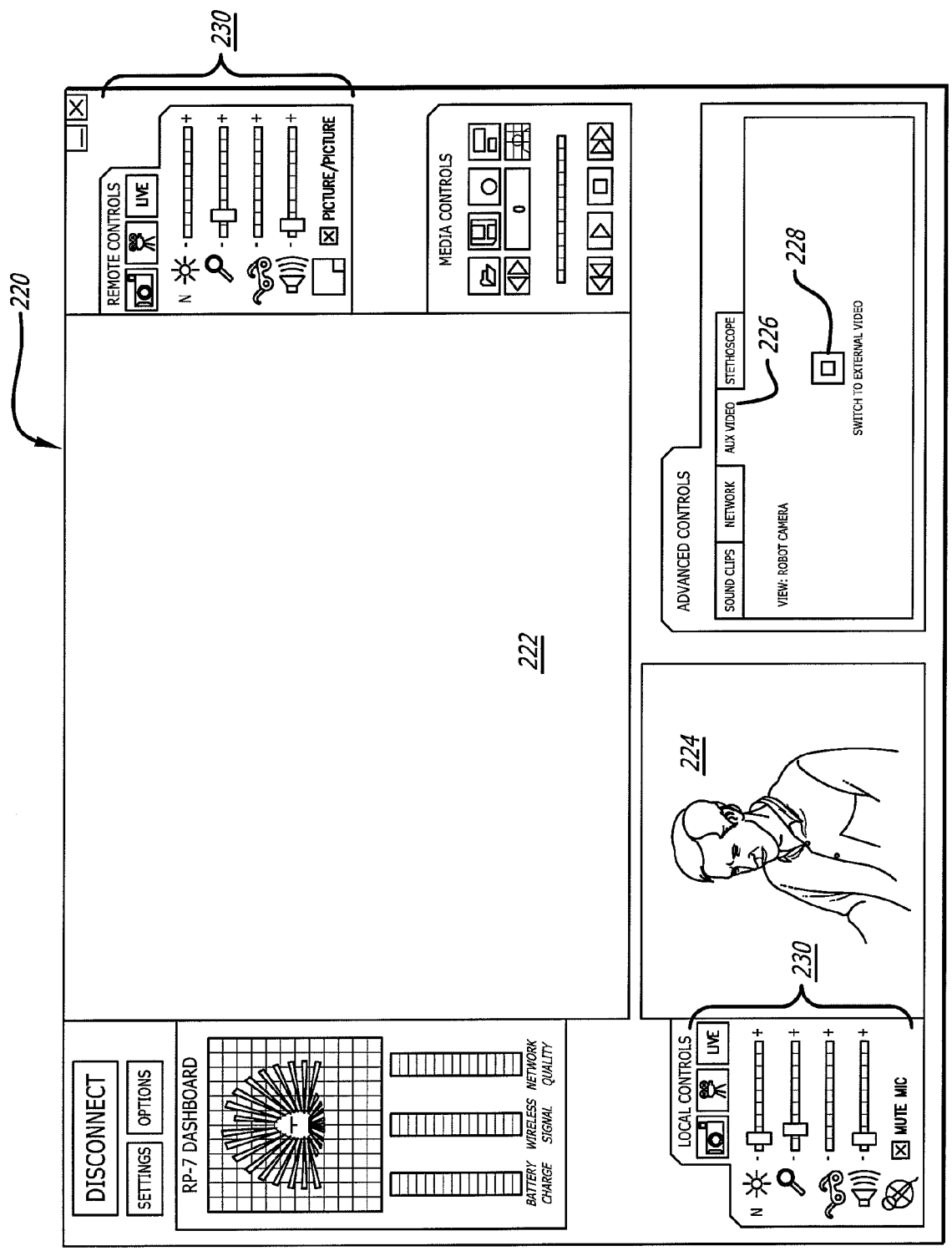
FIG. 4 is a graphical user interface of a remote station.

FIG. 4 shows a display user interface ("DUI") 220 that can be displayed at the remote station 16. The DUI 220 may include a robot view field 222 that displays a video image provided by one of the cameras 40 or 42, or one of the video devices 72 at the robot location. The DUI 220 may include a station view field 224 that displays a video image provided by the camera of the remote station 16. The DUI 220 may be part of an application program stored and operated by the computer 22 of the remote station 16.

The display user interface 220 may include a Aux Video graphical tab 226 that display a button 228. The button 228 can be selected by a user to display video provided by one of the video devices 72 in the robot view field 222. The interface 220 may have additional graphical icons 230 that allow the user to adjust different parameters of the system such as camera brightness, audio volume, capturing a still picture, etc.

The user can highlight a portion of a non-zoom image to display a zoom image that corresponds to the highlighted area. Additionally, the user can circle, annotate, etc. portions of video with a telestrator function of the system 10.

Figure 5:
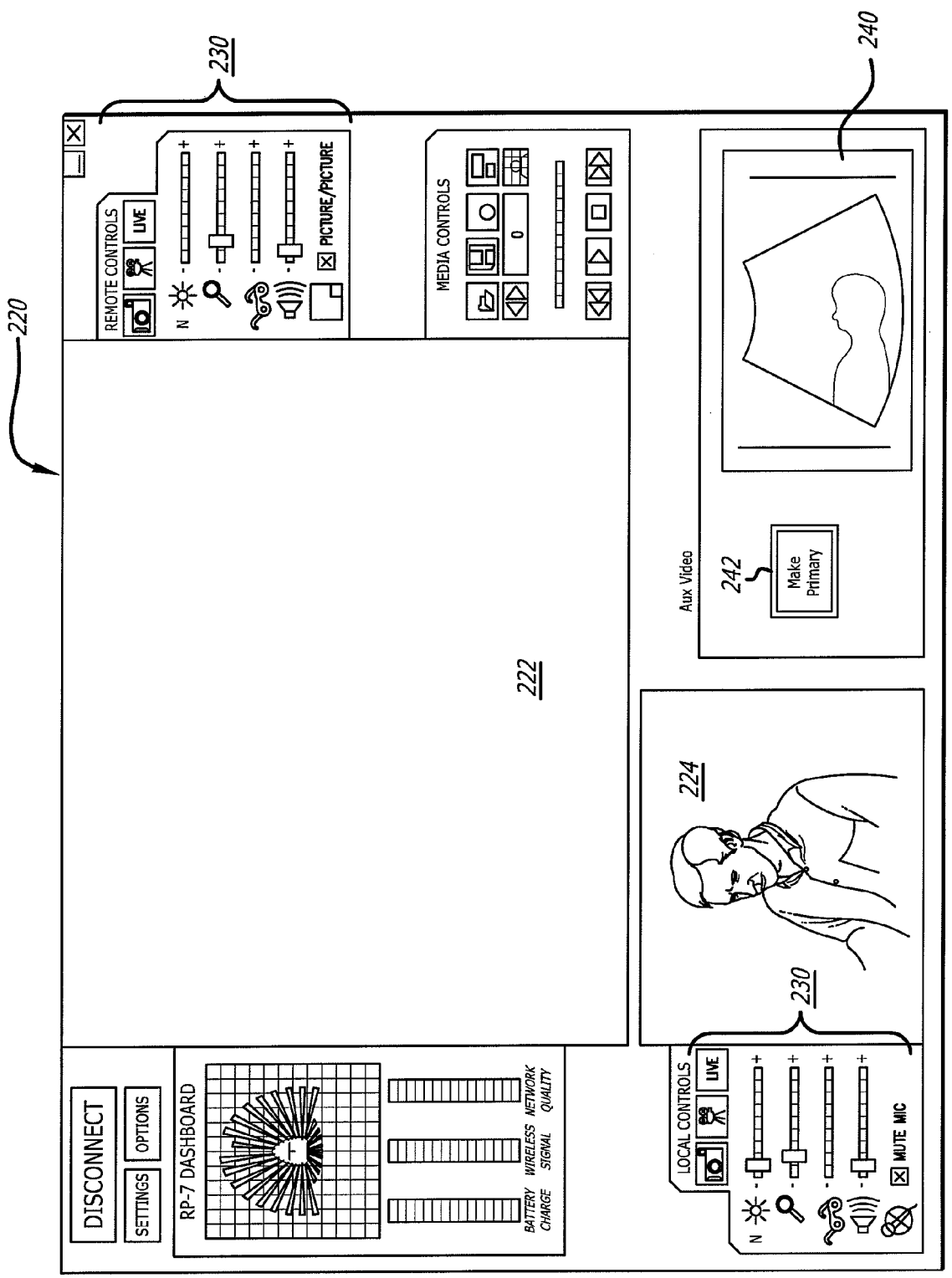
FIG. 5 is the graphical user interface showing a medical image in an auxiliary view field.

The system 10 can be used in a process wherein a medical personnel such as a doctor move the robot 12 adjacent to a patient that is being assisted by another medical personnel such as a nurse. The nurse can plug the ultrasound device into the auxiliary video port of the robot. Plugging the ultrasound device into the robot may cause ultrasound images to be transmitted and displayed within the robot view field 222. Alternatively, the doctor can select graphical button 228 which causes the ultrasound image to be displayed in an auxiliary view field 240 shown in FIG. 5. The auxiliary field 240 may have a graphical button 242 that can be selected to switch the ultrasound image into the robot view field 222 and the images from the robot camera into field 240. When both ultrasound and video images from the robot camera are transmitted to the remote station, the robot may enter a mode wherein the ultrasound images are transmitted at a larger frame size, higher frame rate and higher video compression and the robot camera images are transmitted at a smaller frame size, lower frame rate and lower compression. This mode allocates a higher portion of network bandwidth to the medical images. This mode can be selected through a graphical button (not shown) displayed on the remote control station monitor. The robot camera images and the medical images may also be encrypted. For example, the images may be encrypted with a 128 bit AES encryption with a symmetric key that is exchanged at the start of a session.

During a session where an ultrasound device is coupled to the robot a technician may be located at the robot site in the vicinity of a patient. The technician may move the ultrasound device to different positions on the patient. The images are transmitted to the control station and displayed by the monitor for viewing by a doctor. The doctor and technician can discuss the ultrasound images through the control station and robot. The doctor may also provide instructions on where to place the ultrasound device. For example, the doctor can instruct the technician to move the ultrasound device to different locations on a patient. The system allows the doctor to conduct a remote video conference while viewing ultrasound images in real time.

The robot 12 may be placed in a home or a facility where one or more patients are to be monitored and/or assisted. The facility may be a hospital or a residential care facility. By way of example, the robot 12 may be placed in a home where a health care provider may monitor and/or assist the patient. Likewise, a friend or family member may communicate with the patient. The cameras and monitors at both the robot and remote control stations allow for teleconferencing between the patient and the person at the remote station(s).

The robot 12 can be maneuvered through the home or a facility by manipulating the input device 32 at a remote station 16. The robot 10 may be controlled by a number of different users. To accommodate for this the robot may have an arbitration system. The arbitration system may be integrated into the operating system of the robot 12. For example, the arbitration technique may be embedded into the operating system of the high-level controller 150.

By way of example, the users may be divided into classes that include the robot itself, a local user, a caregiver, a doctor, a family member, or a service provider. The robot 12 may override input commands that conflict with robot operation. For example, if the robot runs into a wall, the system may ignore all additional commands to continue in the direction of the wall. A local user is a person who is physically present with the robot. The robot could have an input device that allows local operation. For example, the robot may incorporate a voice recognition system that receives and interprets audible commands.

A caregiver is someone who remotely monitors the patient. A doctor is a medical professional who can remotely control the robot and also access medical files contained in the robot memory. The family and service users remotely access the robot. The service user may service the system such as by upgrading software, or setting operational parameters.

The robot 12 may operate in one of two different modes; an exclusive mode, or a sharing mode. In the exclusive mode only one user has access control of the robot. The exclusive mode may have a priority assigned to each type of user. By way of example, the priority may be in order of local, doctor, caregiver, family and then service user. In the sharing mode two or more users may share access with the robot. For example, a caregiver may have access to the robot, the caregiver may then enter the sharing mode to allow a doctor to also access the robot. Both the caregiver and the doctor can conduct a simultaneous tele-conference with the patient.

The arbitration scheme may have one of four mechanisms; notification, timeouts, queue and call back. The notification mechanism may inform either a present user or a requesting user that another user has, or wants, access to the robot. The timeout mechanism gives certain types of users a prescribed amount of time to finish access to the robot. The queue mechanism is an orderly waiting list for access to the robot. The call back mechanism informs a user that the robot can be accessed. By way of example, a family user may receive an e-mail message that the robot is free for usage. Tables I and II, show how the mechanisms resolve access request from the various users.

TABLE I

| User | Access Control | Medical Record | Command Override | Software/Debug Access | Set Priority |
| --- | --- | --- | --- | --- | --- |
| Robot | No | No | Yes (1) | No | No |
| Local | No | No | Yes (2) | No | No |
| Caregiver | Yes | Yes | Yes (3) | No | No |
| Doctor | No | Yes | No | No | No |
| Family | No | No | No | No | No |
| Service | Yes | No | Yes | Yes | Yes |

TABLE II

| | | Requesting User | | | |
| --- | --- | --- | --- | --- | --- |
| | | Local | Caregiver | Doctor | Family | Service |
| Current User | Local | Not Allowed | Warn current user of pending user Notify requesting user that system is in use Set timeout | Warn current user of pending user Notify requesting user that system is in use Set timeout = 5 m | Warn current user of pending user Notify requesting user that system is in use Set timeout = 5 m Call back | Warn current user of pending user Notify requesting user that system is in use No timeout Call back |

TABLE II-continued

| | | Requesting User | | | |
|---|---|---|---|---|---|
| | Local | Caregiver | Doctor | Family | Service |
| Caregiver | Warn current user of pending user. Notify requesting user that system is in use. Release control | Not Allowed | Warn current user of pending user Notify requesting user that system is in use Set timeout = 5 m Queue or callback | Warn current user of pending user Notify requesting user that system is in use Set timeout = 5 m | Warn current user of pending user Notify requesting user that system is in use No timeout Callback |
| Doctor | Warn current user of pending user Notify requesting user that system is in use Release control | Warn current user of pending user Notify requesting user that system is in use Set timeout = 5 m | Warn current user of pending user Notify requesting user that system is in use No timeout Callback | Notify requesting user that system is in use No timeout Queue or callback | Warn current user of pending user Notify requesting user that system is in use No timeout Callback |
| Family | Warn current user of pending user Notify requesting user that system is in use Release Control | Notify requesting user that system is in use No timeout Put in queue or callback | Warn current user of pending user Notify requesting user that system is in use Set timeout = 1 m | Warn current user of pending user Notify requesting user that system is in use Set timeout = 5 m Queue or callback | Warn current user of pending user Notify requesting user that system is in use No timeout Callback |
| Service | Warn current user of pending user Notify requesting user that system is in use No timeout | Notify requesting user that system is in use No timeout Callback | Warn current user of request Notify requesting user that system is in use No timeout Callback | Warn current user of pending user Notify requesting user that system is in use No timeout Queue or callback | Not Allowed |

The information transmitted between the station 16 and the robot 12 may be encrypted. Additionally, the user may have to enter a password to enter the system 10. A selected robot is then given an electronic key by the station 16. The robot 12 validates the key and returns another key to the station 16. The keys are used to encrypt information transmitted in the session.

The robot 12 and remote station 16 transmit commands through the broadband network 18. The commands can be generated by the user in a variety of ways. For example, commands to move the robot may be generated by moving the joystick 32 (see FIG. 1). The commands are preferably assembled into packets in accordance with TCP/IP protocol. Table III provides a list of control commands that are generated at the remote station and transmitted to the robot through the network.

TABLE III

| | Control Commands | |
|---|---|---|
| Command | Example | Description |
| drive | drive 10.0 0.0 5.0 | The drive command directs the robot to move at the specified velocity (in cm/sec) in the (x, y) plane, and turn its facing at the specified rate (degrees/sec). |
| goodbye | goodbye | The goodbye command terminates a user session and relinquishes control of the robot |
| gotoHomePosition | gotoHomePosition 1 | The gotoHomePosition command moves the head to a fixed "home" position (pan and tilt), and restores zoom to default value. The index value can be 0, 1, or 2. The exact pan/tilt values for each index are specified in robot configuration files. |
| head | head vel pan 5.0 tilt 10.0 | The head command controls the head motion. It can send commands in two modes, identified by keyword: either positional ("pos") or velocity ("vol"). In velocity mode, the pan and tilt values are desired velocities of the head on the pan and tilt axes, in degree/sec. A single command can include just the pan section, or just the tilt section, or both. |
| keepalive | keepalive | The keepalive command causes no action, but keeps the communication (socket) link open so that a session can continue. In scripts, it can be used to introduce delay time into the action. |

TABLE III-continued

| Control Commands | | |
|---|---|---|
| Command | Example | Description |
| odometry | odometry 5 | The odometry command enables the flow of odometry messages from the robot. The argument is the number of times odometry is to be reported each second. A value of 0 turns odometry off. |
| reboot | reboot | The reboot command causes the robot computer to reboot immediately. The ongoing session is immediately broken off. |
| restoreHeadPosition | restoreHeadPosition | The restoreHeadPosition functions like the gotoHomePosition command, but it homes the head to a position previously saved with gotoHomePosition. |
| saveHeadPosition | saveHeadPosition | The saveHeadPosition command causes the robot to save the current head position (pan and tilt) in a scratch location in temporary storage so that this position can be restored. Subsequent calls to "restoreHeadPosition" will restore this saved position. Each call to saveHeadPosition overwrites any previously saved position. |
| setCameraFocus | setCameraFocus 100.0 | The setCameraFocus command controls focus for the camera on the robot side. The value sent is passed "raw" to the video application running on the robot, which interprets it according to its own specification. |
| setCameraZoom | setCameraZoom 100.0 | The setCameraZoom command controls zoom for the camera on the robot side. The value sent is passed "raw" to the video application running on the robot, which interprets it according to its own specification. |
| shutdown | Shutdown | The shutdown command shuts down the robot and powers down its computer. |
| stop | stop | The stop command directs the robot to stop moving immediately. It is assumed this will be as sudden a stop as the mechanism can safely accommodate. |
| timing | Timing 3245629 500 | The timing message is used to estimate message latency. It holds the UCT value (seconds + milliseconds) of the time the message was sent, as recorded on the sending machine. To do a valid test, you must compare results in each direction (i.e., sending from machine A to machine B, then from machine B to machine A) in order to account for differences in the clocks between the two machines. The robot records data internally to estimate average and maximum latency over the course of a session, which it prints to log files. |
| userTask | userTask "Jane Doe" "Remote Visit" | The userTask command notifies the robot of The current user and task. It typically is sent once at the start of the session, although it can be sent during a session if the user and/or task change. The robot uses this information for record-keeping. |

Table IV provides a list of reporting commands that are generated by the robot and transmitted to the remote station through the network.

TABLE IV

| Reporting Commands | | |
|---|---|---|
| Command | Example | Description |
| abnormalExit | abnormalExit | This message informs the user that the robot software has crashed or otherwise exited abnormally. Te robot software catches top-level exceptions and generates this message if any such exceptions occur. |

TABLE IV-continued

Reporting Commands

| Command | Example | Description |
| --- | --- | --- |
| bodyType | bodyType 3 | The bodyType message informs the station which type body (using the numbering of the mechanical team) the current robot has. This allows the robot to be drawn correctly in the station user interface, and allows for any other necessary body-specific adjustments. |
| driveEnabled | driveEnabled true | This message is sent at the start of a session to indicate whether the drive system is operational. |
| emergencyShutdown | emergencyShutdown | This message informs the station that the robot software has detected a possible "runaway" condition (an failure causing the robot to move out of control) and is shutting the entire system down to prevent hazardous motion. |
| odometry | odometry 10 20 340 | The odometry command reports the current (x, y) position (cm) and body orientation (degrees) of the robot, in the original coordinate space of the robot at the start of the session. |
| sensorGroup | group_data | Sensors on the robot are arranged into groups, each group of a single type (bumps, range sensors, charge meter, etc.) The sensorGroup message is sent once per group at the start of each session. It contains the number, type, locations, and any other relevant data for the sensors in that group. The station assumes nothing about the equipment carried on the robot; everything it knows about the sensors comes from the sensorGroup messages. |
| sensorState | groupName state data | The sensorState command reports the current state values for a specified group of sensor. The syntax and interpretation for the state data is specific to each group. This message is sent once for each group at each sensor evaluation (normally several times per second). |
| systemError | systemError driveController | This message informs the station user of a failure in one of the robot's subsystems. The error_type argument indicates which subsystem failed, including driveController, sensorController, headHome. |
| systemInfo | systemInfo wireless 45 | This message allows regular reporting of information that falls outside the sensor system such as wireless signal strength. |
| text | text "This is some text" | The text string sends a text string from the robot to the station, where the string is displayed to the user. This message is used mainly for debugging. |
| version | version 1.6 | This message identifies the software version currently running on the robot. It is sent once at the start of the session to allow the station to do any necessary backward compatibility adjustments. |

The processor 154 of the robot high level controller 150 may operate a program that determines whether the robot 12 has received a robot control command within a time interval. For example, if the robot 12 does not receive a control command within 2 seconds then the processor 154 provides instructions to the low level controller 150 to stop the robot 12. Although a software embodiment is described, it is to be understood that the control command monitoring feature could be implemented with hardware, or a combination of hardware and software. The hardware may include a timer that is reset each time a control command is received and generates, or terminates, a command or signal, to stop the robot.

The remote station computer 22 may monitor the receipt of video images provided by the robot camera. The computer 22 may generate and transmit a STOP command to the robot if the remote station does not receive or transmit an updated video image within a time interval. The STOP command causes the robot to stop. By way of example, the computer 22 may generate a STOP command if the remote control station does not receive a new video image within 2 seconds. Although a software embodiment is described, it is to be understood that the video image monitoring feature could be implemented with hardware, or a combination of hardware and software. The hardware may include a timer that is reset each time a new video image is received and generates, or terminates, a command or signal, to generate the robot STOP command.

While certain exemplary embodiments have been described and shown in the accompanying drawings, it is to be understood that such embodiments are merely illustrative of and not restrictive on the broad invention, and that this invention not be limited to the specific constructions and arrangements shown and described, since various other modifications may occur to those ordinarily skilled in the art.

What is claimed is:

1. A remote controlled robot system, comprising:
   a robot with a robot monitor, and a robot camera that captures a patient image of a patient, said robot having an auxiliary video port, said robot including a microphone and a speaker;
   a medical image device that is coupled to said auxiliary video port and can capture a medical image of a patient; and,
   a remote control station that has a microphone and a speaker and transmits commands to control said robot, said remote control station includes a control station camera that captures a medical image of a medical personnel and a control station monitor that displays a display user interface, said display user interface simultaneously displays the patient image captured by said robot camera in a robot view field, said medical personnel image in a station view field, and said medical image in an auxiliary view field, wherein a doctor located at said remote control station can conduct a video conference with a technician located at said robot while viewing the patient image and the medical image.

2. The system of claim 1, wherein said medical image device is an ultrasound device.

3. The system of claim 1, wherein said medical image device is an otoscope.

4. The system of claim 1, wherein said medical image device is an echocardiogram.

5. The system of claim 1, further comprising a broadband network coupled to said robot and said remote control station.

6. The system of claim 1, wherein said robot camera and said robot monitor are mechanically coupled to always move together.

7. The system of claim 1, wherein a larger portion of a network bandwidth is allocated for the medical image than the patient image.

8. A method for reviewing images of a patient, comprising:
   moving a robot that has a microphone, a speaker, a monitor and a camera adjacent to a patient with commands from a remote control station that includes a microphone, a speaker, a camera and a monitor;
   capturing a patient image of a patient with the robot camera;
   transmitting the patient image to the remote control station;
   displaying the patient image on the remote control station monitor;
   moving a medical image device relative to a patient by a technician;
   capturing a medical personnel image of the patient with the medical image device, the captured medical image being provided to the robot;
   transmitting the medical image from the robot to the remote control station;
   capturing a medical personnel image of a medical personnel with a remote control station camera;
   displaying the medical image on a display user interface of the remote control station monitor simultaneously with the display of the patient image and the remote station medical personnel image; and, conducting a video conference between the technician and a doctor, while the doctor views the medical image and the patient image.

9. The method of claim 8, wherein the medical image device captures ultrasound images.

10. The method of claim 8, further comprising selecting a graphical input of a graphical user interface displayed by the remote control station monitor to display the medical image.

11. The method of claim 8, wherein the medical image is transmitted at a higher frame rate than the patient image.

* * * * *